US010295543B2

(12) United States Patent
Howell et al.

(10) Patent No.: US 10,295,543 B2
(45) Date of Patent: *May 21, 2019

(54) METHOD OF OVERCOMING THERAPEUTIC LIMITATIONS OF NON-UNIFORM DISTRIBUTION OF RADIOPHARMACEUTICALS AND CHEMOTHERAPY DRUGS

(71) Applicant: Rutgers, The State University of New Jersey, New Brunswick, NJ (US)

(72) Inventors: Roger W. Howell, Millington, NJ (US); John M. Akudugu, Bellville (ZA); Jordan B. Pasternack, Morganville, NJ (US); Venkata S. Neti, Branchburg, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 459 days.

This patent is subject to a terminal disclaimer.

(21) Appl. No.: 15/066,347

(22) Filed: Mar. 10, 2016

(65) Prior Publication Data

US 2016/0258963 A1 Sep. 8, 2016

Related U.S. Application Data

(60) Continuation of application No. 14/526,041, filed on Oct. 28, 2014, now Pat. No. 9,804,167, and a continuation-in-part of application No. 14/444,391, filed on Jul. 28, 2014, now abandoned, and a continuation-in-part of application No. 13/953,414, filed on Jul. 29, 2013, now abandoned, said application No. 14/526,041 is a division of application No. 13/315,775, filed on Dec. 9, 2011, now Pat. No. 8,874,380.

(60) Provisional application No. 61/859,060, filed on Jul. 26, 2013, provisional application No. 61/676,614, filed on Jul. 27, 2012, provisional application No. 61/466,151, filed on Mar. 22, 2011, provisional application No. 61/421,491, filed on Dec. 9, 2010.

(51) Int. Cl.
G01N 33/60 (2006.01)
G01N 33/50 (2006.01)
A61K 31/704 (2006.01)
A61K 51/04 (2006.01)
A61K 51/10 (2006.01)

(52) U.S. Cl.
CPC .......... *G01N 33/60* (2013.01); *A61K 31/704* (2013.01); *A61K 51/0402* (2013.01); *A61K 51/1051* (2013.01); *G01N 33/5008* (2013.01); *G01N 33/5011* (2013.01)

(58) Field of Classification Search
CPC .................................................... G01N 33/60

USPC ........................................................ 702/19
See application file for complete search history.

(56) References Cited

U.S. PATENT DOCUMENTS

| 4,816,567 A | 3/1989 | Cabilly et al. |
| 4,997,815 A | 3/1991 | Perrine et al. |
| 5,229,275 A | 7/1993 | Goroff |
| 5,545,806 A | 8/1996 | Lonberg et al. |
| 5,545,807 A | 8/1996 | Surani et al. |
| 5,563,059 A | 10/1996 | Alak et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,591,669 A | 1/1997 | Krimpenfort et al. |
| 5,641,870 A | 6/1997 | Rinderknecht et al. |
| 5,733,743 A | 3/1998 | Johnson et al. |
| 5,869,046 A | 2/1999 | Presta et al. |
| 5,871,907 A | 2/1999 | Winter et al. |
| 5,872,215 A | 2/1999 | Osbourne et al. |
| 5,885,793 A | 3/1999 | Griffiths et al. |
| 5,962,255 A | 10/1999 | Griffiths et al. |
| 6,140,471 A | 10/2000 | Johnson et al. |
| 6,225,447 B1 | 5/2001 | Winter et al. |
| 6,291,650 B1 | 9/2001 | Winter et al. |
| 6,327,490 B1 | 12/2001 | Spetz |
| 6,432,673 B1 | 8/2002 | Gao et al. |
| 6,492,160 B1 | 12/2002 | Griffiths et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,699,473 B2 | 3/2004 | Raisch et al. |
| 6,908,764 B2 | 6/2005 | Czichos et al. |

(Continued)

FOREIGN PATENT DOCUMENTS

| EP | 404097 | 6/1990 |
| EP | 1 319 708 A2 | 6/2003 |

(Continued)

OTHER PUBLICATIONS

Akudugu et al., "Changes in lognormal shape parameter guide design of patient-specific radiochemotherapy cocktails, " J Nucl Med., (2011) vol. 52, pp. 642-649.

(Continued)

*Primary Examiner* — Jerry Lin

(74) *Attorney, Agent, or Firm* — Fox Rothschild LLP

(57) ABSTRACT

Therapeutic compositions for treating diseased cells such as cancer cells in a patient, formulated from a plurality of therapeutic agents selected from radiopharmaceuticals, chemotherapeutic agents and radionuclide labeled antibodies. Methods for predicting the response of an individual patient's cells to therapeutic intervention are also disclosed.

23 Claims, 21 Drawing Sheets

(56) References Cited

U.S. PATENT DOCUMENTS

| | | | |
|---|---|---|---|
| 7,326,572 | B2 | 2/2008 | Fisk et al. |
| 7,763,466 | B2 | 7/2010 | Keller et al. |
| 8,283,168 | B2 | 10/2012 | Keller et al. |
| 8,748,171 | B2 | 6/2014 | Keller et al. |
| 8,815,591 | B2 | 8/2014 | Keller et al. |
| 8,951,792 | B2 | 2/2015 | Heins et al. |
| 2002/0146678 | A1 | 10/2002 | Benvenisty |
| 2003/0003573 | A1 | 1/2003 | Rambhatle et al. |
| 2003/0027331 | A1 | 2/2003 | Yan et al. |
| 2003/0109035 | A1 | 6/2003 | Asashima et al. |
| 2003/0130496 | A1 | 7/2003 | Winter et al. |
| 2004/0121464 | A1 | 6/2004 | Rathjen et al. |
| 2005/0054102 | A1 | 3/2005 | Wobus et al. |
| 2006/0003446 | A1 | 1/2006 | Keller et al. |
| 2012/0106703 | A1 | 5/2012 | Roy et al. |
| 2012/0107234 | A1 | 5/2012 | Pedersen et al. |
| 2013/0123567 | A1 | 5/2013 | Agamaite et al. |

FOREIGN PATENT DOCUMENTS

| | | | |
|---|---|---|---|
| WO | 1993/011161 | | 6/1993 |
| WO | 1994/025591 | | 11/1994 |
| WO | 1997/017852 | | 5/1997 |
| WO | 01/53465 | A1 | 7/2001 |
| WO | 02/29012 | A1 | 4/2002 |
| WO | 03/083088 | A2 | 10/2003 |
| WO | 0383088 | A3 | 12/2003 |
| WO | 2005063971 | A2 | 7/2005 |
| WO | 2005/097980 | A2 | 10/2005 |
| WO | 2005097990 | A1 | 10/2005 |
| WO | 0597980 | A3 | 12/2007 |

OTHER PUBLICATIONS

Akudugu et al., "Flow cytometry-assisted Monte Carlo simulation predicts clonogenic survival of cell populations with lognormal distributions of radiopharmaceuticals and anticancer drugs," Int J Radiat Biol., (2011) vol. 88, pp. 286-293 (Abstract only).

Brennan et al., "Preparation of bispecific antibodies by chemical recombination of monoclonal immunoglobulin G1 fragments," Science, (1985) vol. 229, p. 81-83 (Abstract only).

Carter et al., "High level *Escherichia coli* expression and production of a bivalent humanized antibody fragment," Biotechnology (1992) vol. 10, pp. 163-167 (Abstract only).

Deutscher, editor, "Guide to Protein Purification" in Methods in Enzymology (1990) Academic Press, Inc. (Synopsis only).

Freshney, "Culture of Animal Cells: A Manual of Basic Technique," 2nd Ed. (1987), Liss, Inc. New York, NY (Synopsis only).

Georgiou, et al., "Display of heterologous proteins on the surface of microorganisms: From the screening of combinatorial libraries to live recominant vaccines," Nature Biotechnology, (1997) vol. 15, pp. 29-34.

Graham et al., "Manipulation of adenovirus vector," in "Gene Transfer and Expression Protocols," The Humana Press Inc., Clifton, NJ (1991) E. J. Murray, editor, vol. 7, pp. 109-128 (Synopsis of book only).

Hanes and Pluckthun, "In Vitro selection and evolution of functional proteins by using ribosome display," Proc. Nat. Acad. Sci. (1997) vol. 94, p. 4937-4942.

Hollinger et al., "'Diabodies': small bivalent and bispecific antibody fragments," Proc. Natl. Acad. Sci. USA, (1993) vol. 90, pp. 6444-6448 (Abstract only).

Innis et al. (editors), "PCR Protocols: A Guide to Methods and Applications," (1990) Academic Press, San Diego, CA (Synopsis of book only).

Jakobovits et al., "Germ-line transmission and expression of a human-derived yeast artificial chromosome," Nature, (1993) vol. 362, No. 6417, pp. 255-258 (Abstract only).

Jakobovits et al., "Analysis of homozygous mutant chimeric mice: deletion of the immunoglobulin heavy-chain joining region blocks B-cell development and antibody production," Proc. Natl Acad Sci, USA, (1993) vol. 90, pp. 2551-2555.

Jones et al., "Replacing the complementarity-determining regions in a human antibody with those from a mouse," Nature, (1986) vol. 321, No. 6069, pp. 522-525 (Abstract only).

Kabat et al., "Sequences of Proteins of Immunological Interest," 5th Ed. Public Health Service, National Institutes of Health Bethesda, Md. (1991) (Abstract only).

Kieke, et al., "Isolation of anti-T cell receptor scFv mutants by yeast surface display," Protein Engineering, (1997) vol. 10, pp. 1303-1310.

Morimoto et al., "Single-step purification of F(ab')2 fragments of mouse momoclonal antibodies (immunoglobulins G1) by hydrophobic interaction high performance liquid chromotography using TSKgel Phynel-5PW," Journal of Biochemical and Biophysical Methods, (1992) vol. 24, No. 1-2, pp. 107-117 (Abstract only).

Morrison et al., "Chimeric human antibody molecules: Mouse antigen-binding domains with human constant region domains" Proc. Natl. Acad. Sci. USA, (1984) vol. 81, pp. 6851-6855.

Pluckthun et al., "The Pharmacology of Monoclonal Antibodies," (1994) Rosenburg and Moore eds, Springer-Verlag, New York, vol. 113, pp. 269-315.

Reichmann et al., "Reshaping human antibodies for therapy," Nature, (1988) vol. 332; No. 6162; pp. 323-327.

Sambrook et al., Molecular Cloning: A Laboratory Manual, (1989) Cold Spring Harbor Laboratory Press (Description only).

Vaughn, et al., "Human Antibodies with Sub-nanomolar Affinities Isolated form a Large Non-immunized Phage Display Library," Nature Biotechnology, (1996) vol. 14, pp. 309-314 (Abstract only).

Verhoeyen et al., "Reshaping human antibodies: grafting an antilysozyme activity," Science (1988), vol. 239, pp. 1534-1536 (Abstract only).

Zapata et al., "Engineering linear F(ab')2 fragments for efficient production in *Escherichia coli* and enhanced antiproliferative activity," Protein Eng. (1995) vol. 8, Issue 10, pp. 1057-1062 (Abstract only).

Bruggemann et al., "Designer mice: the production of human anitbody repertoires in transgenic animals," Year Immuno., (1993) vol. 7, p. 33-40.

Goeddel (editor), "Gene Expression Technology: Methods in Enzymology," vol. 185, (1991) Academic Press, San Diego, CA.

Li et al., "Feasibility of Eradication of Breast Cancer Cells Remaining in Postlumpectomy Cavity and Draining Lymph Nodes Following Intracavity Injectin of Radioactive Immunoliposomes" Molecular Pharmaceutics, 2012, vol. 9, pp. 2513-2522.

Brink (Cells Tissues Organs, 2008, vol. 188, p. 9-22).

Stem Cells: Scientific Progress and Future Research Directions. Department of Human Services. Jun. 2001. Chapter 4: The Adult Stem Cell., pp. 23-42.

Ito et al., Cultivation of hepatitis C virus in primary hepatocyte culture from patients with chrinic hepatitis C results in release of high titre infectious virus, Journal of General Virology 77:1043-1054, 1996.

Abe et al., Molecular and Embryological Characterization of a New Transgene-Induced Null allele of mouse Brachyury locus, Mamalian Genome 2000, vol. 11, pp. 238-240, Spring-Verlag New York Inc.

Srinivas et al., Cre reporter strains produced by targeted insertion of EYFP and ECFP into the ROSA26 locus. BMC Development 2001, vol. 1:4, online journal.

Ansari-Lari et al., A gene-rich cluster between the CD4 and triosephophate isonerase genes at human chromosome 12p13. Genome Research 1996, vol. 6, No. 4, pp. 314-316.

Weinstein et al, The winged-helix transcription factor HNF-3beta is required for notochord development in the mouse embryo, Cell 1994, vol. 78, pp. 575-588.

Johansson et al., "Evidence for Involvement of Activin A and Bone Morphogenetic Protein 4 in Mammalian Mesoderm and Hematopoietic Development," Molecular and Cellular Biology (Jan. 1995); vol. 15, No. 1: pp. 141-151.

Dellow et al., "Identification of novel, cardiac-restricted transcription factors binding to a CACC-box within the human cardiac troponin I promoter," Cardiovascular Research (2001): vol. 50: pp. 24-33.

(56) References Cited

OTHER PUBLICATIONS

Clozel et al., "Specific Binding of Endothelin on Human Vascular Smooth Muscle Cells in Culture," (May 1989); vol. 83: pp. 1758-1761.
Abe et al., "Endoderm-specific Gene Expression in Embyronic Stem Cells Differentiated to Embryoid Bodies.", Exp Cell Res., Nov. 1996, vol. 229, No. 1, pp. 27-34, especially p. 26, 28, 32 and 33.
Schuldiner, et al., "Effects of eight growth factors on the differentiation of cells derived from human embryonic stem cells", PNAS, Oct. 10, 2000, vol. 97, No. 21, pp. 11307-11312.
Gamer et al., Autonomous Endodermal Determination in Xenopus: Regulation of Expression of the Pancreatic Gene X1Hbox 8, (Dev. Biol., 1995, vol. 171, pp. 240-251).
Boucher et al., (2000) Int. J. Dev. Biol, vol. 44, pp. 279-288.
Keller et al., "Hematopoietic Commitment During Embryonic Stem Cell Differentiation in Culture" Jan. 1993, Molecular and Cellular Biology, vol. 13, No. 1, pp. 473-486.
Kispert et al., (1993) The EMBO Journal, vol. 12; pp. 3211-3220.
Reyes et al., (2001) Blood, vol. 98, pp. 2615-2625.
Tada et al., (2005) Development, vol. 132, pp. 4363-4374.
Wiles et al., (1999) Experimental Cell Research, vol. 247; pp. 241-248.
Muhr et al., "Assignment of Early Caudal Identity to Neural Plate Cells by a Signal from Caudal Paraxial Mesoderm,", Neuron, vol. 19, pp. 487-502, Sep. 1987.
Rodaway et al., Medendoderm: An Ancient Germ Layer, Cell, vol. 105, pp. 169-172, Apr. 20, 2001, Copyright 2001 by Cell Press.
Rodaway et al., "Induction of the mesendoderm in the zebrafish germ ring by yolk cell-derived TGF-.beta. family signals and discrimination of mesoderm and endoderm by FGF", Development vol. 126, pp. 3067-3078 (1999), Printed in Great Britain.
Slager et al., "Secretion of Transforming Growth Factor-.beta. Isoforms by Ebryonic Stem Cells: Isoform and Latency Are Dependent on Direction of Differentiation", Journal of Cellular Physiology, vol. 156, pp. 247-256, (1993).
Brachyury, JCLS, vol. 43, No. 10, pp. 1347-1354;1420, Aug. 1998, Printed in Japan.
Wilson et al., Chimeric analysis of T (Brachyury) gene function, Development, vol. 117, pp. 1321-1331 (1993), Printed in Great Britain.
Fehling et al. (2003) Development 130:4217-4227.
Rambhatle et al. (2003) Cell Transplantation 12:1-11.
Yasunaga et al. (2005) Induction and Monitoring of Definitive and Visceral Endoderm Differentiation of Mouse ES Cells, Nature Biotechnology, 23, pp. 1542-1550.
Rashbass et al. Nature 353:348-351, Sep. 26, 1991.
Conquet. Neuropharmacology 34(8):865-870, 1995.
Mao et al. Blood 97:324-326, 2001.
Reyes et al. (2001) Blood 98:2615-2625.
Tada et al. (2005) Development 132:4363-4374.
Takahashi et al. (1998) Protein, Nucleic Acid and enzyme 43:1347-1354.
Lagasse et al. (2000) Nature Medicine 6:1229-1234.
Asashima et al., Transplantation Now, 2000, 13: 330-336.
Edwards et al., Genome Res., 1996, 6: 226-223.
Elges et al., Current Biol., 2001, 11: 514-518.
Guan et al., Cytotechnology, 1996, 30: 211-226.
Hamazaki et al., FEBS Lett., 2001, 497: 15-19.
Kimelman et al., Curr.Opin.Genetics Dev., 2000, 10: 350-356.
David et al., Blood, 2008, 111: 1876-1884.
Hockmeyer et al., Nature Biotechnology, 2009, 27: 851-858.
Urbach et al., Stem Cells, 2004, 22: 635-641.
Zou et al., Cell Stem Cell, 2009, 5: 97-110.
Zwaka et al., Nature Biotechnology, 2008, 21: 319-321.
Assady et al. "Insulin Production by Human Embryonic Stem Cells." Diabetes 50: 1691-1697 (Aug. 2001).
Davidson et al. "Exogenus FGF-4 Can Suppress Anterior Development in the Mouse Embryo during Neurulation and Early Organogenesis." Developmental Biology 221: 41-52. (2000).
Borrebaeck, Ed., "Antibody Engineering (Breakthroughs in Molecular Biology)," Oxford University Press USA, 1995, 2nd Ed. (Summary).
Smith, A. G., "Embryo-Derived Stem Cells: Of Mice and Men", Annu. Rev. Cell Dev. Biol. 17: 435-462. (2001).
Ang, et al. "The formation and maintenance of the definitive endoderm lineage in the mouse: involvement of the HNF3/forkhead proteins." Development 119: 1301-1315. (1993).
Srinivas, et al. Cre reporter strains produced by targeted insertion of EYFP and ECFP into the ROSA26 locus. BMC Development (2001) 1:4. <<http://www.biomedcentral.com/1471-213X1/4>> Last accessed Dec. 20, 2007.

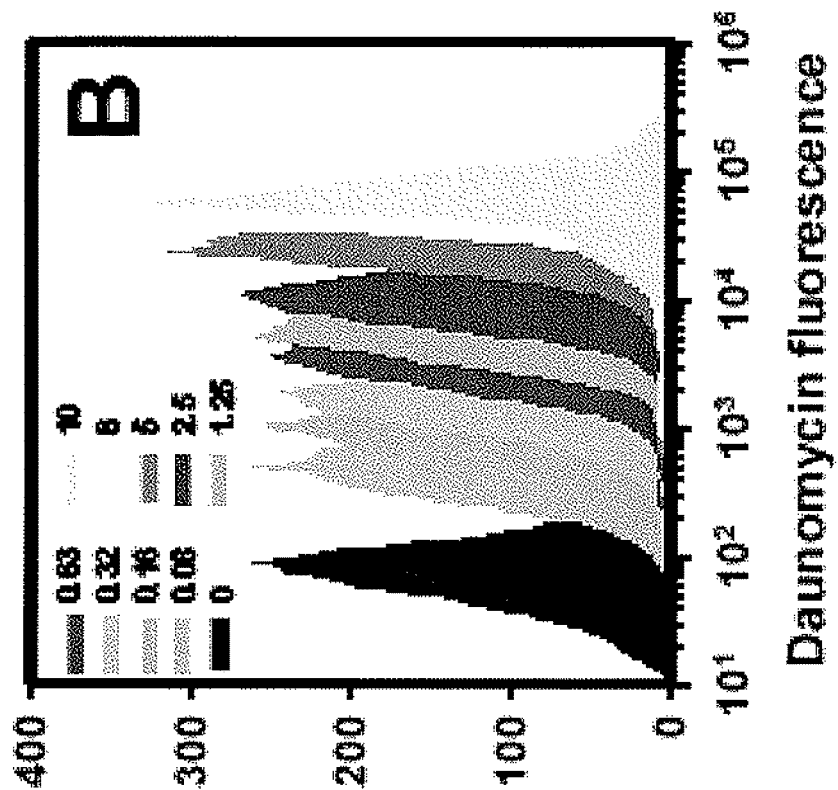
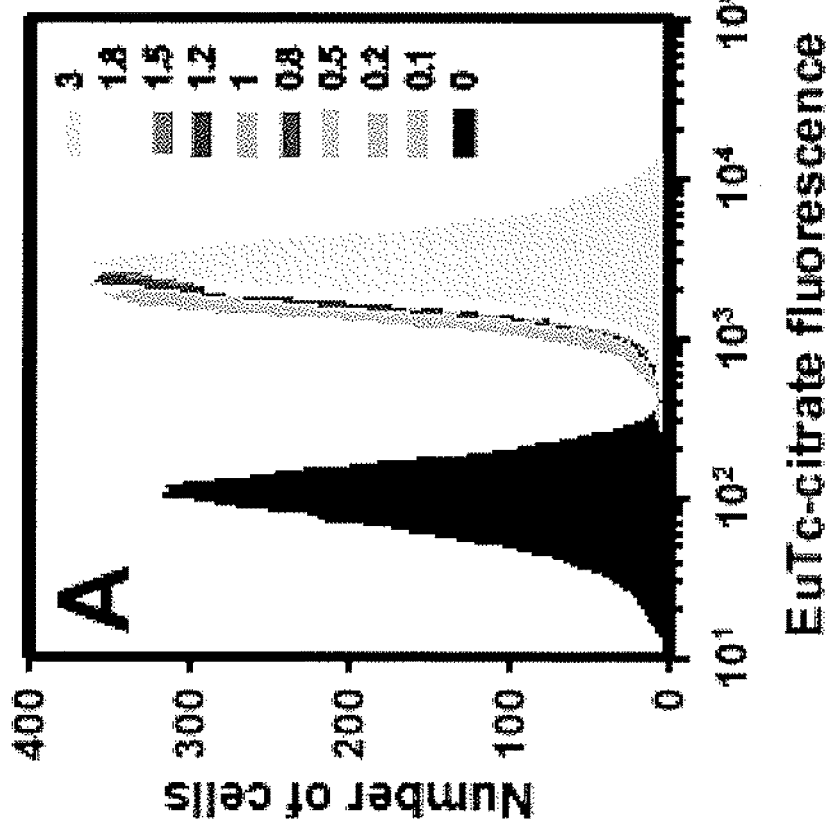
FIGURE 1A
FIGURE 1B

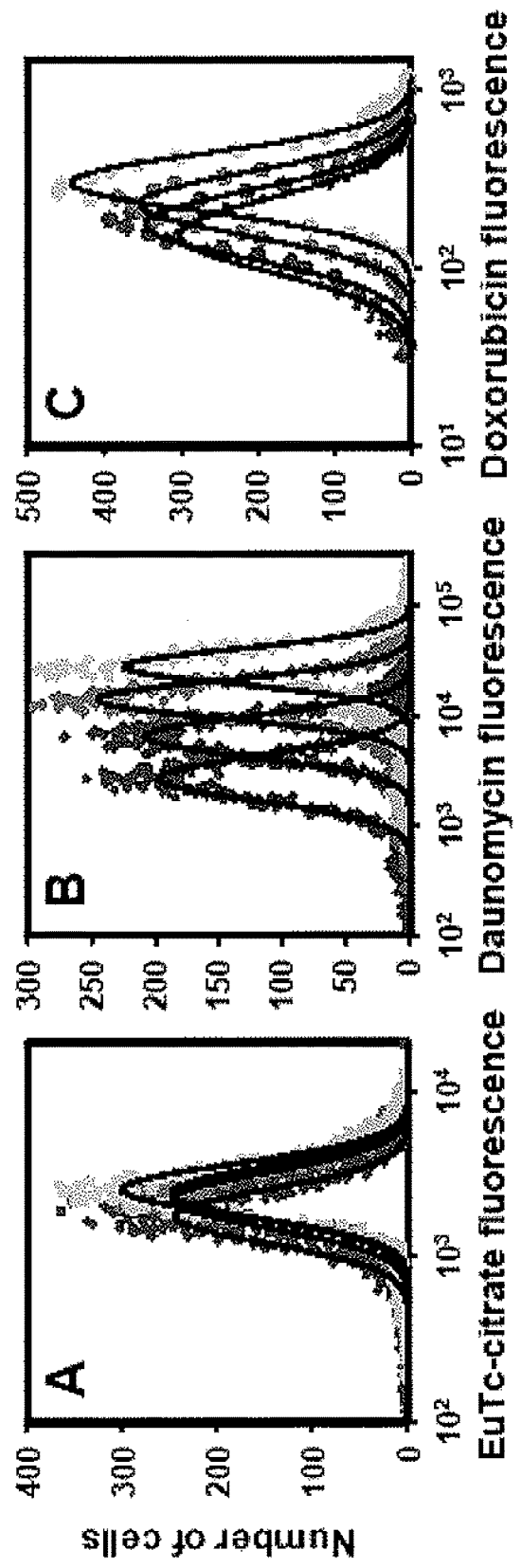

STEP 1

Flow cytometry measurement of drug uptake $I_i$

STEP 1

Flow cytometry measurement of drug uptake $I_i$

FIGURE 9A
Daunomycin
FIGURE 9B
Doxorubicin
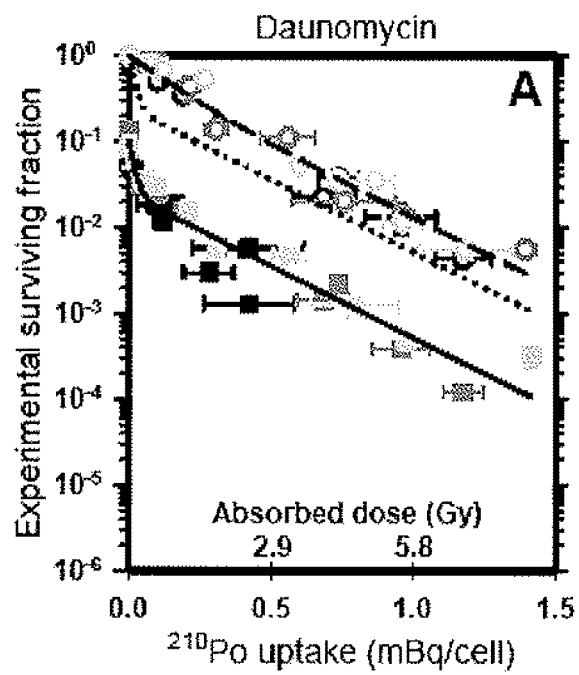
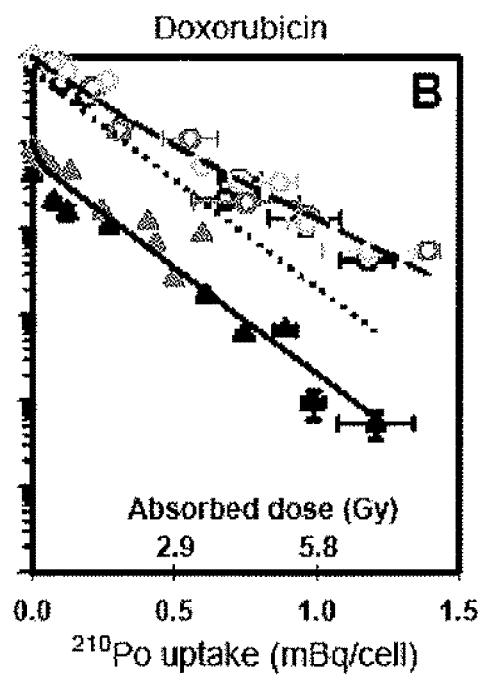
FIGURE 10A
Daunomycin
FIGURE 10B
Doxorubicin
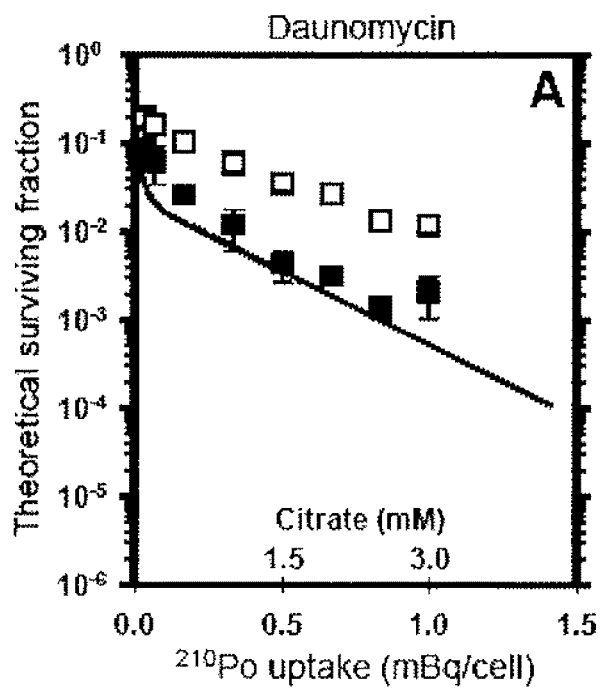
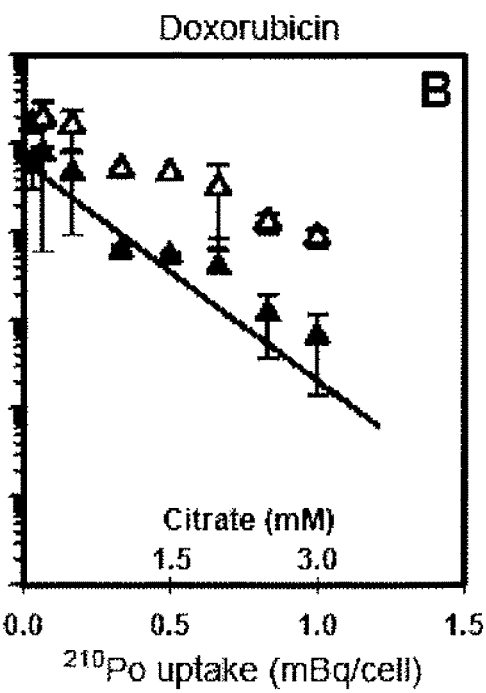

METHOD OF OVERCOMING THERAPEUTIC LIMITATIONS OF NON-UNIFORM DISTRIBUTION OF RADIOPHARMACEUTICALS AND CHEMOTHERAPY DRUGS

CROSS-REFERENCE TO RELATED APPLICATIONS

The present application is a continuation-in-part under 35 U.S.C. § 120 of U.S. patent application Ser. No. 14/444,391 (the '391 Application) filed Jul. 28, 2014, U.S. patent application Ser. No. 13/953,414 (the '414 Application) filed Jul. 29, 2013, and U.S. patent application Ser. No. 14/526,041 (the '041 Application), filed Oct. 28, 2014. The '391 Application claims priority benefit under 35 U.S.C. § 119(e) of U.S. Provisional Application No. 61/859,060 filed Jul. 26, 2013. The '414 Application claims priority benefit under 35 U.S.C. § 119(e) of U.S. Provisional Application No. 61/676,614 filed Jul. 27, 2012. The '041 Application is a Division of U.S. patent application Ser. No. 13/315,775, filed Dec. 9, 2011, now U.S. Pat. No. 8,874,380, which in turn claims priority benefit under 35 U.S.C. § 119(e) of both U.S. Provisional Application No. 61/446,151, filed Mar. 22, 2011 and U.S. Provisional Application No. 61/421,491, filed Dec. 9, 2010. The disclosures of all foregoing references are incorporated by reference herein in their entireties.

STATEMENT REGARDING FEDERALLY SPONSORED RESEARCH OR DEVELOPMENT

The invention was made with government support under Contract No. R01 CA083838 awarded by NIH/NCI and Contract No. 5R25CA019536-32 awarded by NIH. The government has certain rights in the invention.

FIELD OF THE INVENTION

The present invention relates to a novel method for formulating cocktails of therapeutic agents and predicting the optimal amount of each constituent radiopharmaceutical and/or chemotherapy agent to administer to a patient, by, in some embodiments, determining the amount of each agent bound to each cell in a targeted population of cells, the level of cell saturation of these agents and by simulating cell death and surviving fraction, preferably using Monte Carlo methods.

BACKGROUND OF THE INVENTION

The use of chemotherapeutic drugs as an adjuvant to external beam radiotherapy, surgery, or other treatment modalities is common practice for the treatment of a wide variety of solid tumors. This approach has demonstrated some success in the management of certain cancers. The rationale for combining chemotherapeutic agents with external beam radiotherapy is to radiosensitize the irradiated tumor tissue and/or to target subpopulations of malignant cells that have metastasized from the primary lesion demarcated for beam therapy. Although the tradition of chemoradiotherapy has been practiced for decades and shows promise, some attempts have not succeeded in demonstrating either an added therapeutic benefit or a reduction of normal tissue toxicity. In another approach, radiolabeled chemotherapy agents have been used in an attempt to achieve enhanced cytotoxicity both in human cancer cells and apparently normal hamster fibroblasts. Chemotherapy has also been combined with radioimmunotherapy.

One limitation of chemoradiotherapy is the frequent lack of interaction between chemotherapeutics and ionizing radiation. This often leads to escalation of radiation and drug doses, which in turn, results in elevated normal tissue toxicity. Moreover, lack of specificity of chemotherapy drugs for tumor tissue can result in an insignificant difference in toxicity towards malignant and normal tissues thereby providing no added therapeutic benefit compared to surgery and radiation alone. Despite these limitations, chemoradiotherapy often provides considerable therapeutic benefit. However, observed inconsistencies in treatment outcomes may be due to the widely varying chemotherapeutic drug concentrations employed and radiation absorbed doses achieved. In addition, there is evidence demonstrating that optimization of radiation dose and drug concentration, and the time sequence for administering drugs and radiation play important roles in treatment responses both in vitro and in vivo. Also, regardless of the quality of radiation used, the wide variability in drug toxicity in normal cells of different histologies has to be considered in favor of the most sensitive tissue in chemoradiotherapy. Unfavorable outcomes in therapies involving the use of chemotherapy drugs and radiopharmaceuticals have been attributed to insufficient tumor specificity, poor tumor vascularization, and non-uniformities in agent distribution at the macroscopic, cellular, and subcellular levels. Determination of drug and radionuclide incorporation at the single-cell level has been difficult. As such, estimation of intracellular chemotherapy drug concentration and intracellular radioactivity, which is required to determine radiation absorbed dose to the cell, has largely been restricted to the macroscopic level. Accordingly, it has been difficult to establish a relationship between therapeutic agent incorporation and biologic response.

It has now been discovered that, even in situations where there is optimum perfusion and no diffusion barriers, cellular incorporation of radionuclides and chemotherapeutic drugs is not only non-uniform, but is also lognormal. This strongly suggests that the limited success in chemo-radiotherapy of primary solid tumors and metastatic disease is likely due to this lognormal phenomenon, in which minute subpopulations of cells take up very little or no therapeutic agent. Repopulation by these subpopulations could mask a possible treatment benefit and result in an even more resistant neoplastic form. Thus, to enhance tumor response, there continues to be a need to address the non-uniform, lognormal distribution of chemotherapy drugs and radiopharmaceuticals. Using a quantitative immunofluorescence-based approach, it has now been demonstrated in a 3-dimensional culture system that concomitant measurement of radiopharmaceutical uptake and biologic response in individual cells within a population can be used to predict the response of subpopulations of cells, and ultimately of the entire population. Such capabilities now allow the design of more effective cocktails for clinical applications.

BRIEF SUMMARY OF THE INVENTION

One aspect of the present invention relates to a novel method for predicting the optimal amount of radiopharmaceutical and chemotherapy agents to administer to a patient, by determining the level of cell saturation. U.S. Pat. No. 8,874,380, incorporated by reference here in its entirety, discloses a method of predicting the response of an individual patient's disease to therapeutic intervention with radiopharmaceuticals, chemotherapeutics, targeted therapeutics such as radiolabeled monoclonal antibodies, or other agents, in which cellular incorporation of therapeutic agents is measured in the target cell population on a cell-by-cell basis using a flow cytometer. The resulting fluorescence spectra are fitted to the lognormal probability density function to obtain the lognormal shape parameter, σ, also known as the standard deviation, for each treated sample. Changes in the lognormal shape parameter, σ, upon exposure of the cells to increasing drug concentrations correlate with changes in the shape of the cell survival curve, and therefore can identify the optimal drug concentration for use in a drug cocktail. The surviving fraction of a target cell population exposed to the therapeutic agent can be predicted using a flow-cytometry assisted Monte Carlo simulation that accounts for the lognormal characteristics of the distribution; and the optimal cocktail of therapeutic drugs can be identified by exposing target cells to combinations of drugs. The optimal concentration of each drug is identified by employing flow cytometry to simultaneously measure the uptake of each drug, then simulating the surviving fraction of the target population using the Monte Carlo simulation and using the simulated results to identify the combination of drugs that affords the optimum degree of killing of the target cells.

It has now been discovered that the surviving fraction of a target cell population exposed to therapeutic agents can be predicted using a flow-cytometry assisted simulation, such as a Monte Carlo simulation, without fitting the fluorescence spectra to the lognormal probability density function and then accounting for the non-uniform distribution in the simulation.

Therefore, according to one aspect of the present invention, a therapeutic composition for treating diseased cells in a patient is provided in which the relative concentration of therapeutic agents most effective to treat the diseased cells is determined by the method of the present invention. The composition contains a plurality of therapeutic agents selected from radiopharmaceuticals, chemotherapeutic agents and radionuclide labeled antibodies, wherein the selection of and the relative concentrations of the therapeutic agents in the composition is determined by a method including the steps of:

(a) exposing populations of the diseased cells to increasing concentrations of combinations of the therapeutic agents, to increasing concentrations of the individual therapeutic agents, or both;

(b) measuring the incorporation by cellular uptake of the therapeutic agents or the therapeutic agent combinations;

(c) plotting the number of cells vs the amount of incorporated therapeutic agents to obtain distribution plots for the cell populations;

(d) predicting the surviving fractions of the cell populations employing a simulation that that uses the therapeutic agent distribution plots and a function that expresses the probability that a given cell will survive a given amount of an incorporated therapeutic agent; and (e) selecting the therapeutic agent combination and relative concentration of each agent within the selected combination predicted to be most lethal.

According to one embodiment of this aspect of the invention, the therapeutic agents are selected from a plurality of radionuclide labeled antibodies, and the relative concentrations of the radionuclide labeled antibodies in the composition is determined by a method including the steps of:

(a) exposing populations of the diseased cells to increasing concentrations of combinations of the radionuclide labeled antibodies, to increasing concentrations of the individual radionuclide labeled antibodies, or both;

(b) measuring the incorporation by cellular uptake of the radionuclide labeled antibodies or the radionuclide labeled antibody combinations;

(c) plotting the number of cells vs the amount of incorporated antibodies to obtain distribution plots for the cell populations;

(d) predicting the surviving fractions of the cell populations employing a simulation that that uses the calculated incorporation the antibodies in each cell and a function that expresses the probability that a given cell will survive upon incorporating a cellular radiation dose characteristic of the radionuclide of the incorporated antibody; and (e) selecting the radionuclide labeled antibody combination and relative concentration of each antibody within the selected combination predicted to be most lethal.

According to one embodiment, the simulation is a Monte Carlo simulation. In another embodiment, the Monte Carlo simulation is a flow-cytometry assisted Monte Carlo simulation.

Another embodiment of the invention is directed to a method for predicting the response of an individual patient's cells, which preferably comprise cancer cells, to therapeutic intervention, comprising the steps of:

a) exposing populations of the diseased cells to increasing concentrations of combinations of the therapeutic agents, to increasing concentrations of the individual therapeutic agents, or both;

(b) measuring the incorporation by cellular uptake of the therapeutic agents or the therapeutic agent combinations;

(c) plotting the number of cells vs the amount of incorporated therapeutic agents to obtain distribution plots for the cell populations; and (d) predicting the surviving fractions of said cell populations employing a simulation that that uses the therapeutic agent distribution plots and a function that expresses the probability that a given cell will survive a given amount of an incorporated therapeutic agent.

According to one embodiment, the method further comprises the step of (e) selecting the therapeutic agent combination and relative concentration of each agent within the selected combination predicted to be most lethal.

According to one embodiment, the therapeutic agents are selected from a plurality of radionuclide labeled antibodies, and the relative concentrations of the radionuclide labeled antibodies in the composition is determined by a method including the steps of:

(a) exposing populations of the diseased cells to increasing concentrations of combinations of the radionuclide labeled antibodies, to increasing concentrations of the individual radionuclide labeled antibodies, or both;

(b) determining the number of antibodies bound to individual diseased cells;

(c) predicting the surviving fractions of the cell populations employing a simulation that that uses the therapeutic agent distribution plots and a function that expresses the probability that a given cell will survive a given amount of an incorporated therapeutic agent; and (d) selecting the therapeutic agent combination and relative concentration of each agent within the selected combination predicted to be most lethal.

According to one embodiment, determining the number of antibodies bound to individual diseased cells is accomplished by the steps of (i) measuring fluorescence intensity and (ii) calculating absorbed dose to each cell According to one embodiment, measuring fluorescence intensity utilizes Bang's beads.

According to one embodiment, the simulation comprises a Monte Carlo simulation. In a further embodiment, the Monte Carlo simulation is modified to account for specific activity of the antibodies. In yet a further embodiment, the Monte Carlo simulation is further modified to account for the calculated absorbed dose to each cell.

BRIEF DESCRIPTION OF THE DRAWINGS

FIGS. 1A, 1B and 1C shows the distribution of cellular uptake of citrate, daunomycin, and doxorubicin by V79 cells in a suspension culture. Displayed are representative flow cytometry generated histograms of cellular fluorescence intensity after treatment with 0-3 mmol/L EuTc-citrate (FIG. 1A), 0-10 µmol/L daunomycin (FIG. 1B), or 0-10 µmol/L doxorubicin (FIG. 1C).

FIGS. 2A, 2B and 2C shows the least squares fits of the flow cytometry fluorescence intensity histograms to a log-normal probability distribution. The histograms correspond to (FIG. 2A) EuTc-citrate, (FIG. 2B) daunomycin, and (FIG. 2C) doxorubicin.

FIG. 4A displays $^{210}$Po-citrate for three independent experiments, SF plotted against absorbed dose to the cell nucleus, intracellular $^{210}$Po activity, and net mean fluorescence intensity (MFI) of the europium tetracycline-citrate complex. Data plotted are from three independent experiments. Curve represents a least squares fit of the data to a single component exponential function. FIG. 4B displays daunomycin (open square), SF plotted against extracellular drug concentration and against net MFI of the drug. FIG. 4C displays doxorubicin (open triangle), SF plotted against extra-cellular drug concentration and against net MFI of the drug. Curves for daunomycin and doxorubicin represent least-squares fits to a two-component exponential function. For $^{210}$Po-citrate, horizontal and vertical error bars represent SE of mean cellular activity and surviving fraction of triplicate measurements, respectively. For daunomycin and doxorubicin, horizontal and vertical error bars represent SE of Net MFI and surviving fraction for three independent experiments.

FIG. 5A: In STEP 1, flow cytometry was used to obtain fluorescence intensity of EuTc-citrate ($^{210}$Po-citrate), daunomycin, and doxorubicin in individual V79 cells in a suspension culture. The distribution of measured cellular fluorescence intensities is shown in (A) 0.1-3 mM citrate, (B) 0-10 µM daunomycin, or (C) 0-10 µM doxorubicin. FIG. 5B: After calculating the probability of survival $P_i(I'_i)$ for the $i^{th}$ cell based on the normalized fluorescence intensity $I'_i$ (STEP 2), a random number $RAND_i$ (0<$RAND_i$≤1) was generated as depicted in STEP 3 by the dice. If $RAND_i$<$P_i$ ($I'_i$), then the cell was scored as a survivor, otherwise it was considered dead (STEP 4). A surviving cell is represented by a blossoming tree with leaves, while a dead cell is depicted by a tree without leaves. By repeating STEPS 1-4 for every cell in each population, the surviving fraction for any sample population was calculated as illustrated in STEP 5.

FIG. 8A: In STEP 1, flow cytometry is used to obtain a fluorescence intensity dot-plot of the treated cells. FIG. 8B: STEP 2 calculates the probability $P(I'_{i1},I'_{i2})$ that the $i^{th}$ cell survives treatment with Agents 1 and 2, based on the respective normalized fluorescence intensities and $I'_{i1}$ and $I'_{i2}$. A random number $RAND_i$ (0<$RAND_i$≤1) is then generated as depicted in STEP 3 by the dice. If $RAND_i$<$P(I'_{i1},I'_{i2})$, then the cell is scored as a survivor, otherwise it is considered dead (STEP 4). By repeating STEPS 1-4 for every cell, the surviving fraction for any sample population is calculated as illustrated in STEP 5.

FIGS. 9A and 9B displays the surviving fraction of V79 cells after treatment with graded amounts of $^{210}$Po-citrate in the absence or presence of: (FIG. 9A) 0.63 µM daunomycin or (FIG. 9B) 2.50 µM doxo-rubicin. Three independent experiments (○ $^{210}$Po-citrate; ■ $^{210}$Po-citrate+daunomycin; ▲ $^{210}$Po-citrate+doxorubicin). Dashed lines represent least-squares fits of data for $^{210}$Po-citrate to a 1-component exponential function. Solid curves represent least-squares fits of data for the combined treatment to 2-component exponential functions. Correction of the combined treatment curves for drug toxicity yielded the dotted curves. Horizontal and vertical error bars represent SE of mean cellular activity and surviving fraction of triplicate measurements, respectively. Some error bars are smaller than the symbols.

FIGS. 10A and 10B displays the comparison of Monte Carlo simulated cell survival (symbols) with experimental clonogenic cell survival (solid curves) of V79 cells after treatment with combinations of (FIG. 10A) $^{210}$Po-citrate+ 0.63 µM daunomycin or (FIG. 10B) $^{210}$Po-citrate+2.50 µM doxorubicin. The experimental survival curves are least squares fits of the data presented in FIG. 9. Open and closed symbols represent Monte Carlo simulations of cell survival when the agents are assumed to act independently and interactively, respectively. Error bars represent the SE for simulated surviving fraction based on fluorescence data from two independent experiments for each cocktail. Some error bars are smaller than the symbols.

(FIG. 16C) shows Rescaled vertical axis for 3.0 µg/mL plot to emphasize a subpopulation of cells with low Ab4 binding. Antibodies were armed with $^{211}$At at specific activity of 4.25× 10$^{15}$ Bq/mol. Data represent combination of 3 experiments, with exception of Ab3 (2 experiments).

DETAILED DESCRIPTION OF PREFERRED EMBODIMENTS

Figure 1C:
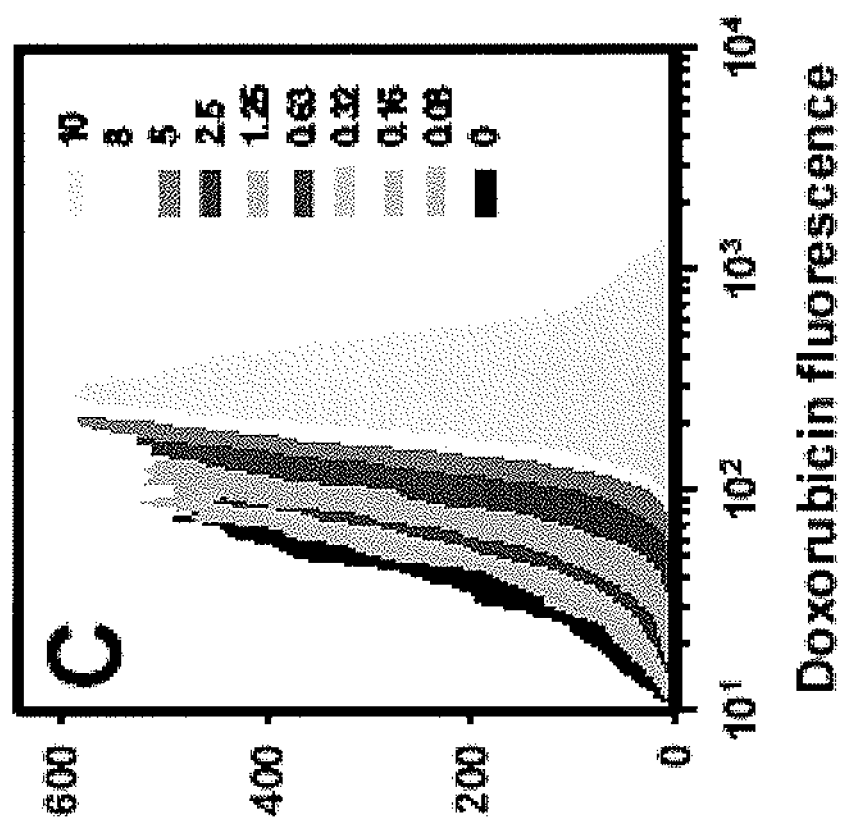

The therapeutic significance of non-uniform incorporation of chemotherapy drugs and radiopharmaceuticals by cancer cells has been recognized as an issue of long standing in the art. Yet, until U.S. Pat. No. 8,874,380, the impact of lognormal drug distributions on the capacity of an agent to sterilize a population of cells has not been previously recognized. For a working Monte Carlo simulation, see Example 1 infra. U.S. Pat. No. 8,874,380 discloses that a small lognormal shape parameter ($\sigma$) implies a narrow distribution profile, and a approaches zero when all cells incorporate the same amount of agent. On the other hand, a large a signifies a wide spread in distribution, and agent incorporation may range from very low (potentially non-toxic) to high (lethal). The ubiquity of lognormal drug distributions has now been demonstrated by using flow cytometry to assess the distribution of radionuclides, for example, $^{210}$Po-citrate, and pharmaceutical agents, for example, daunomycin, and doxorubicin. Equally important is the discovery that changes in the value of a as a function of increasing drug concentration parallel marked changes in the shapes of the corresponding clonogenic cell survival curves. Further, surprisingly it has now been discovered that experimental lognormal distributions (i.e. individual drug uptake on a cell-by-cell basis) can be used to accurately predict the saturation that is observed in experimental cell survival-curves (e.g. two-component exponential curves). This saturation has now been observed repeatedly in studies on the lethal effects of non-uniform distributions of radioactivity. Furthermore, theoretical studies now show that lognormal distributions can lead to such two-component exponential survival curves in both monolayer and three-dimensional tissue constructs.

The overall biological response must be influenced by the magnitude of the mean cellular drug uptake and the degree of heterogeneity in agent distribution. Therefore, a change in the capacity of an agent to sterilize a cell population is related to both the change in width of the distribution and the peak-shift as the agent concentration increases. While the former is a measure of the broadness of a distribution profile of the agent among a cell population and can be represented by the lognormal shape parameter, $\sigma$, the latter is a shift in the lognormal scale parameter µ which is an indication of cells accumulating increasing levels of the agent. Changes in $\sigma$ are prognostic of whether a survival curve will exhibit saturation, and that $\sigma$ may guide in the selection of agents for multimodality cocktail design by providing information on agent concentrations at which the first component of cell kill ends. However, the shape parameter only describes the agent distribution profile of the cell population as a whole, but does not provide information on the fate of individual cells of the population.

Surprisingly, it has also now been discovered that clonogenic cell survival can be predicted based only on knowledge of the initial slope of the cell survival curve and information on the distribution of agent incorporation among the treated cell population. For example, the distribution of $^{210}$Po, daunomycin and doxorubicin among populations of Chinese hamster V79 cells was assessed using flow cytometry techniques and used to theoretically model the surviving fraction. Several modeling approaches were compared, including flow-cytometry gating of agent-negative cells, Monte Carlo simulation of cell survival based on the experimental distributions of drug uptake, and Monte Carlo simulation of cell survival based on the more conventional approach of using mean cellular uptake of the drugs.

It has now been demonstrated that Monte Carlo simulation using cellular agent incorporation based on individual cell fluorescence intensity of therapeutic agents is a suitable predictor of cell survival. This flow cytometry based approach, which takes explicit account of the lognormal distribution of cellular uptake of the agents, offers a rapid means for determining treatment response on a cell-by-cell basis, and allows the selection of agents for the design of highly effective therapeutic cocktails that are capable of targeting the diversity in tumor cell populations. Such cocktails can be created not only for treatment of cancer, but also for infectious diseases and other diseases that may be amenable to targeted therapies. Furthermore, this single-cell Monte Carlo technique can be used to resolve difficulties encountered when attempting to predict biological response at the multicellular level using macroscopic mean agent doses.

However, it has also been discovered that the surviving fraction of a target cell population exposed to therapeutic agents can be predicted using a flow-cytometry assisted simulation, such as a Monte Carlo simulation, without fitting the fluorescence spectra to the lognormal probability density function and then accounting for the lognormal characteristics of the distribution in the simulation. The simulation results are then used to identify an effective combination of therapeutic agents in their therapeutically effective amounts.

The biological targets of the method include cells with uncontrolled growth, such as tumor cells, or cells infected with pathogens, including without limitation, bacteria, viruses, prions, and parasites. The biological target may also include stem cells. In a preferred embodiment of the method, the individual patient's cells comprise cancer cells.

The therapeutic agents comprise, without limitation, antibodies, peptides, chemotherapeutics, radiopharmaceuticals, antifungals, antibiotics and other pharmaceuticals.

Any high-speed technique for assaying drug uptake on a cell-by-cell basis, as known in the art, can be used, including, without limitation, microfluidic techniques such as flow cytometry and microfluidic impedance cytometry; laser scanning microscopy; and gas chromatography/mass spectrometry (GC/MS). Preferably, the high-speed technique for assaying therapeutic agent uptake on a cell-by-cell basis comprises flow cytometry. The analytical method used to determine the incorporation of therapeutic agent preferably comprises fluorescence spectroscopy. The fluorescence measurement preferably comprises individual cell fluorescence intensities and the mean fluorescence intensity (MFI).

Preferably, the probability density function is selected from the group of functions consisting of lognormal, normal, Weibull and exponential. The probability function chosen will have some impact on the value of $\sigma$, and therefore will have some impact when determining the optimal concentration from plots of $\sigma$ versus concentration. Most preferably, the probability density function is lognormal. However, the simulation of the surviving fraction can also directly employ the incorporation data (e.g. flow cytometry data) without relying on a lognormal or other function fit to obtain $\sigma$.

The probability function of the plot of surviving cell fraction versus the amount of incorporated therapeutic agent can be any typical dose-response function. Preferably this survival probability function is selected from the group of functions consisting of exponential and linear-quadratic, and is most preferably exponential.

Preferably, the Monte Carlo simulation method comprises flow-cytometry assisted Monte Carlo simulation.

In a further embodiment of the invention, cancer cells are exposed to increasing concentrations of a plurality of therapeutic agents, and the optimal concentration of each drug/agent is identified, and the simulation results are used to identify a combination of therapeutic agents that affords a high degree of killing of the cancer cells. Preferably the degree of killing of the cancer cells is about 99% or greater, more preferably 99.9% or greater, and most preferably 99.99% or greater. The method can also be used to identify a combination of drugs that affords the optimum degree of killing of the cancer cells.

In yet another embodiment of the invention, the method further comprises the step of identifying one or more drugs that can be added to a combination of therapeutic agents to facilitate the killing of subpopulations of cells that would otherwise escape killing by said combination.

Yet another embodiment of the invention comprises a method of high-throughput drug discovery comprising the methods described above for predicting the response of an individual patient's cells to therapeutic intervention. Such an embodiment can be implemented on a high-throughput drug discovery platform. For example, in one embodiment, a tissue sample from a patient would be cultured and loaded into a high-throughput drug discovery device which is coupled to a flow cytometer, numerous combinations from a library of drugs would be screened, and a cocktail specific for the patient at hand would be identified.

A further embodiment of the invention is directed to a computational method for processing the above-indicated data, including flow cytometry data, in order to determine the parameter $\sigma$ and calculate therefrom the optimal dose, or effective dose, of each component of the drug cocktail.

In addition, the above-identified methods can be used in radioimmunochemotherapy to predict the toxicity of cocktails of $\alpha$-emitting radiopharmaceuticals and chemotherapy drugs in a manner that takes into account the effects of lognormal and other nonuniform distributions of agents within cell populations. These agents can interact with one another and cause greater than expected effects based on their single-agent toxicities. The approach is employed advantageously in the selection of agents for the design of highly effective $\alpha$-particle based therapeutic cocktails that are capable of targeting the diversity in tumor cell populations.

The above-identified methods have the capacity to predict clonogenic survival after multi-modality therapy, using flow cytometry-assisted Monte Carlo simulation. It is demonstrated herein that Monte Carlo simulation using cellular agent incorporation based on individual cell fluorescence intensities of therapeutic agents is a suitable predictor of cell survival. This model accounts for the lognormal distribution of cellular uptake of the agents, and is capable of predicting treatment response on a cell-by-cell basis.

Cellular Uptake of $^{210}$Po-Citrate, Daunomycin, and Doxorubicin

Figures 3A, 3B, 3C:
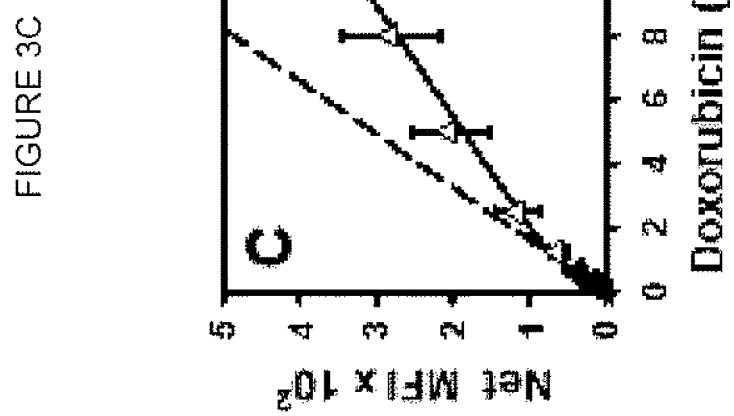
FIG. 3A displays net mean fluorescence intensity (MFI) of europium tetracycline-citrate complex (EuTc-citrate) as a function of extracellular citrate concentration (open circle, solid line) and corresponding mean $^{210}$Po activity per cell (filled circle, dashed line). Lines represent least squares fits of the data to linear functions: MFI=267±16 (mmol/L)$^{-1}$× $C_{cit}$, and MFI=1058±19 (mBq/cell)$^{-1}$×<$a_0$>, where $C_{cit}$ and <$a_0$> are the extracellular citrate concentration and mean cellular activity of $^{210}$Po, respectively.
FIG. 3B displays net MFI of intracellular daunomycin after exposure to low extracellular concentrations (filled square, dashed line) and high concentrations (open square, solid line). Linear least squares fits to the data give MIF$_{dauno}$($C_{dauno}$<0.6 µmol/L)= 5922 (µmol/L)$^1$×$C_{dauno}$ and MFI$_{dauno}$ ($C_{dauno}$>0.6 µmol/L)= 2480 (µmol/L)$^{-1}$×$C_{dauno}$+1161.
FIG. 3C. Net MFI of intracellular doxorubicin after exposure to low extracellular concentrations (filled triangle, dashed line) and high concentrations (open triangle, solid line). Linear least squares fits to the data give MFI$_{doxo}$ ($C_{doxo}$<1 µmol/L)=61 (µmol/ L)$^{-1}$×$C_{doxo}$ and MFI$_{doxo}$($C_{doxo}$>1 µmol/L)=40 (µmol/L)$^{-1}$× $C_{doxo}$+29. For all cases, error bars represent standard error (SE) of three independent experiments.

FIG. 1 shows flow cytometry histograms of the fluorescence intensity of V79 cells that were treated with $^{210}$Po-citrate (FIG. 1A), daunomycin (FIG. 1B), or doxorubicin (FIG. 1C) at concentrations ranging from 0-3 mmol/L, 0-10 µmol/L, and 0-10 µmol/L, respectively. Note that the peaks shift toward higher mean fluorescence as the extracellular concentration of the drug increases. The relatively symmetric nature of the histograms as plotted on a linear-log scale is suggestive of a lognormal distribution of each agent among the cell population. Fluorescence intensity distribution is a lognormal function of the fluorescence intensity I, $$f(I) = \frac{g}{I\sigma\sqrt{2\pi}} e^{-\frac{(\ln I - \mu_I)^2}{2\sigma^2}}, I > 0$$

where $\mu_I$ is the scale parameter, $\sigma$ is the shape parameter, and g is a constant. Least squares fits of the data to this distribution are shown in FIG. 2. Although not observed for EuTc-citrate (FIG. 2A), there is a decrease in the breadth of the lognormal distributions corresponding to daunomycin (FIG. 2B) and doxorubicin (FIG. 2C). Treatment with 0.1 mmol/L citrate resulted in a large increase in mean fluorescence intensity (MFI) from ~163 in untreated samples to ~2000. This can be attributed to the high sensitivity of EuTc for detecting citrate. EuTc is capable of detecting citrate in solutions at concentrations ~1000-fold lower. Since 0.1 mmol/L corresponded to an intracellular $^{210}$Po activity of ~0.02 mBq/cell, which translates to no significant cell kill, background fluorescence of 2000 units was subtracted from the MFI of each sample to obtain a net MFI. The net MFI was then plotted as a function of extracellular citrate concentration (FIG. 3A). With knowledge of the linear correlation between MFI and extracellular citrate concentration, and knowledge of the linear correlation between cellular uptake of $^{210}$Po and extracellular $^{210}$Po-citrate concentration, a similar correlation could be established between MFI and intracellular $^{210}$Po activity (FIG. 3A). A very strong correlation is apparent between cellular incorporation of the vehicle citrate and intracellular $^{210}$Po-activity. Similarly, the fluorescence histograms obtained after treatment of cells with daunomycin and doxorubicin are presented in FIGS. 3B and 3C, respectively. For both drugs, the MFI for the untreated controls were subtracted as background from the MFI of each sample, and the net MFI was plotted against extracellular drug concentration. In each case, net MFI was linearly correlated with drug concentration.

Briefly, flow cytometry was used to quantify their mean fluorescence intensity (MFI) per cell, <I>, as a function of the concentration of the agent in the cell culture medium. The net mean fluorescence intensities per cell, $<I>_{net}$, were determined by subtracting control autofluorescence $<I>_{control}$, Equation (1):

$$<I>_{net} <I> - <I>_{control} \quad (1)$$

The surviving fraction SF of cells exposed to the agent was assessed with a clonogenic survival assay and plotted as a function of several different variables including extracellular concentration, $<I>_{net}$, absorbed dose (Gy), and mean cellular activity (mBq/cell). The resulting survival curves were of a 1- or 2-component exponential form. Analogous to the cellular activity and absorbed dose required to achieve 37% survival, $a_{37}$ and $D_{37}$, the net mean lethal fluorescence intensity of the drug required to achieve 37% survival, $<I>_{net,37}$, can be defined similarly and obtained from plots of SF versus $<I>_{net}$.

Cellular Dosimetry

The absorbed dose to the cell nucleus was determined as known in the art. Since cells were treated with $^{210}$Po-citrate as a single-cell suspension and were subsequently seeded for colony formation, the small contribution of cross-irradiation from neighboring cells in the colony can be ignored because it is essentially counterbalanced by the reduction in self-dose caused by flattening of cells during the colony forming period. The data was least squares fitted to obtain a mean biologic half-time of 11.6 h. Considering the physical half-life of 138 d for $^{210}$Po, this yields an effective half-time $T_e$ of 11.6 h. This $T_e$, the maintenance period of 2.5 h, the subcellular distribution of $^{210}$Po-citrate (28% nucleus, 72% cytoplasm) for V79 cells and published S values, were used to calculate a mean absorbed dose to the cell nucleus of 5.8 Gy/mBq of $^{210}$Po incorporated into the cell.

Toxicity of $^{210}$Po-Citrate, Daunomycin, and Doxorubicin

Figure 4A:
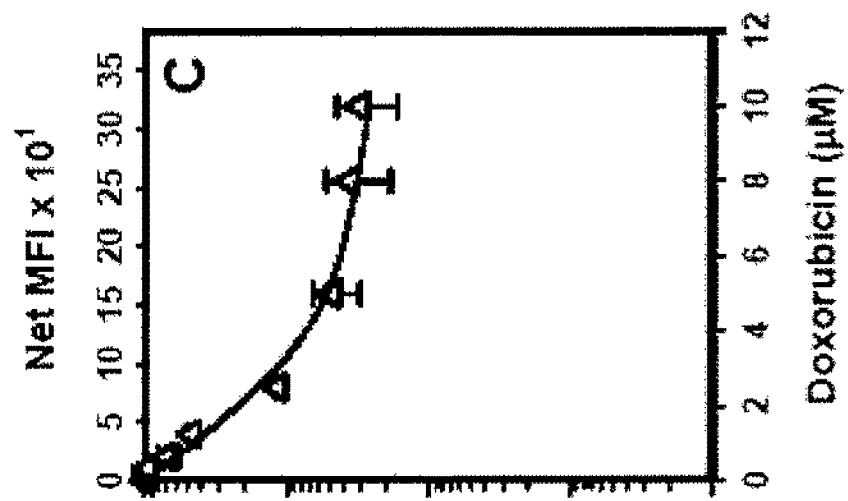
FIGS. 4A, 4B and 4C shows the surviving fraction (SF) of V79 cells after treatment with various agents.
Figure 4B:
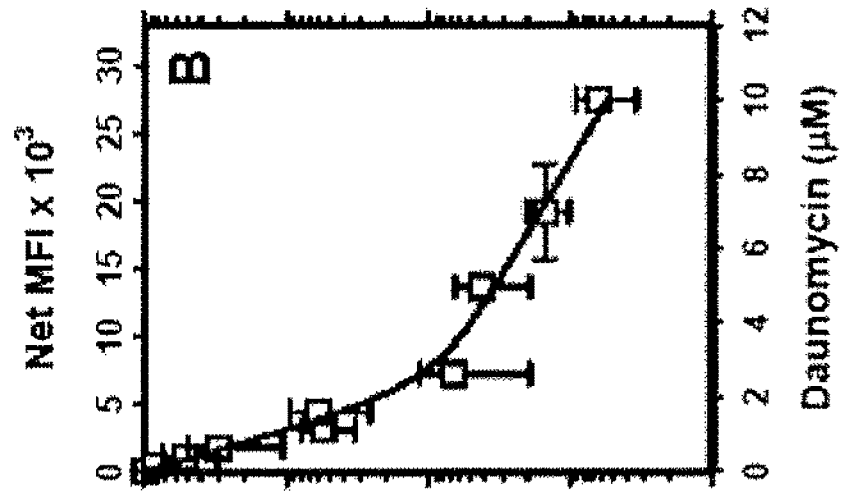
Figure 4C:
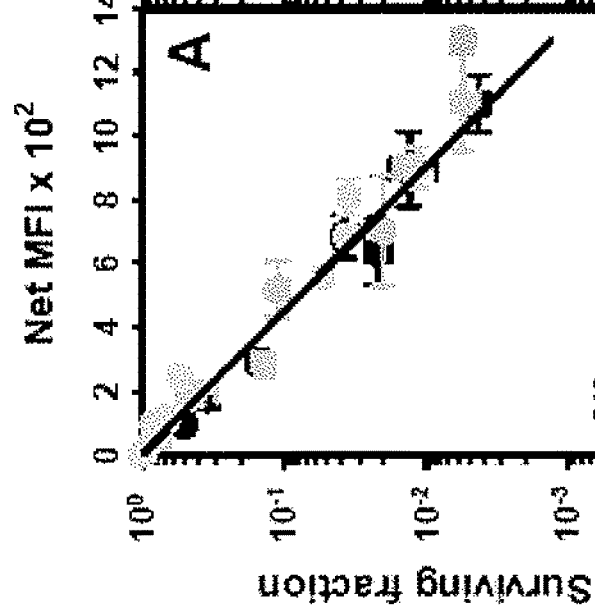

To evaluate $^{210}$Po cytotoxicity, the surviving fraction was plotted as a function of EuTc-citrate net MFI, mean cellular uptake of $^{210}$Po, and mean absorbed dose to the nucleus (FIG. 4A). The data indicate that net MFI of the vehicle (citrate) is a good predictor of $^{210}$Po toxicity within the range of cellular activities employed. The relationships between cell survival and EuTc-citrate net MFI or cellular $^{210}$Po activity can be described by an exponential function SF=exp($-A/A_1$). The relationship between cell survival and drug net MFI (or extracellular concentration) for daunomycin and doxorubicin are illustrated in FIGS. 4B and 4C, respectively. For both drugs, clonogenic survival and cellular drug uptake (as determined by net MFI) are related via two component exponential functions SF=b exp($-A/A_1$)+(1−b) exp($-A/A_2$). A is the intracellular activity of $^{210}$Po-citrate, absorbed dose to the cell nucleus, or drug concentration. Least squares fits of the survival data to this function were performed. The variable b is a fitted parameter.

Role of Agent Distribution in Cellular Toxicity

Figure 6A:
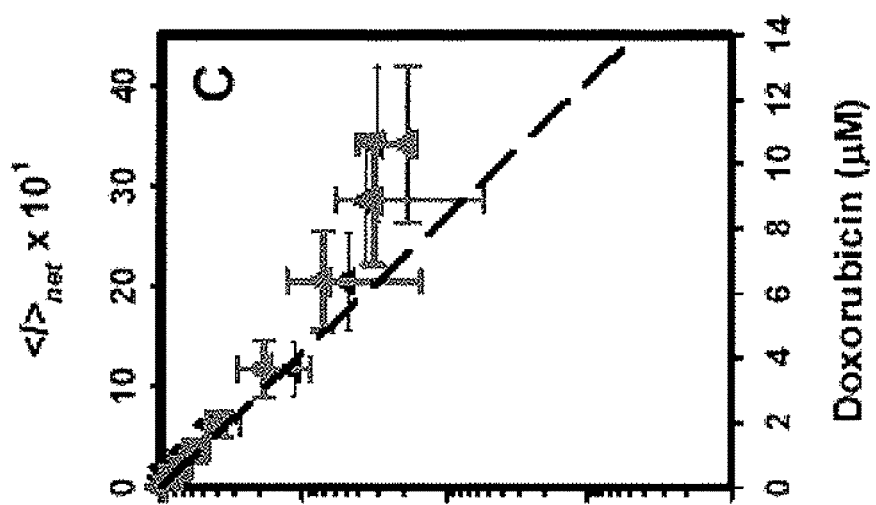
FIGS. 6A, 6B and 6C shows comparison of Monte Carlo simulated cell survival (light symbols) with experimental clonogenic cell survival (black symbols) of V79 cells after treatment with (FIG. 6A) $^{210}$Po-citrate, (FIG. 6B) daunomycin, or (FIG. 6C) doxorubicin. The surviving fraction for $^{210}$Po-citrate are plotted against mean absorbed dose to the cell nucleus, mean intracellular $^{210}$Po activity, and mean fluorescence intensity of the europium tetracycline-citrate complex. Dashed lines represent Monte Carlo simulations of cell survival when every cell in the population is assumed to contain the same amount of drug that corresponds to the mean drug uptake for the respective extracellular concentration (i.e. net mean fluorescence intensity). Error bars represent the SE for <I>$_{net}$ based on fluorescence data from two and three independent experiments for daunomycin and doxorubicin, respectively. Error bars for $^{210}$Po citrate data are smaller than the symbols.

To evaluate the role of the distribution of $^{210}$Po-citrate, daunomycin, and doxorubicin within a cell population in their subsequent toxicity, the fluorescence histograms presented in FIG. 1 were fitted to the lognormal probability density function to obtain the shape parameter a (FIGS. 1 and 2). Although increasing intracellular $^{210}$Po activity did not have an appreciable effect on σ over the entire range of concentrations studied for $^{210}$Po-citrate, increases in extracellular drug concentration had a marked impact on σ for both daunomycin and doxorubicin. The relationship between cell survival and σ for the three agents is illustrated in FIGS. 6 and 7. These plots show that σ for $^{210}$Po-citrate does not change appreciably as the surviving fraction decreases. However, σ for daunomycin and doxorubicin decreases substantially as the surviving fraction decreases.

It is now well established that chemotherapy drugs and radiopharmaceuticals are typically heterogeneously distributed in tissues at the macroscopic, cellular, and subcellular levels. In the case of radiopharmaceuticals, this complicates estimation of cellular absorbed doses based on cellular activities, and causes the relationship between incorporated radioactivity and biologic response to be complex. Several in vitro studies have demonstrated saturation in cell kill with increasing activity per cell following exposure to a variety of radiochemicals, and have attributed the phenomenon to the lognormal nature of the agent distribution. This has also been shown for two chemotherapeutics, daunomycin and doxorubicin. Given the difficulty that is being experienced clinically in terms of sterilizing tumor cell populations with these and other agents, a more thorough understanding of their lognormal distributions and how they affect cell killing is needed to assist in selecting combinations of agents and guide the dosing of the constituent agents. Some enlightenment can be obtained by interpreting the flow cytometric and clonogenic survival studies described above.

FIG. 1 demonstrates that flow cytometry can, under certain circumstances, be used to quantitate intracellular drug concentration. In the present case, this approach is used for EuTc-citrate (surrogate for $^{210}$Po-citrate), and two different chemotherapy drugs, daunomycin and doxorubicin. The distributions of intracellular agent concentration are lognormal (FIG. 2). As shown in FIG. 2A and FIG. 1, the EuTc-citrate is exquisitely lognormal throughout the range of extracellular drug concentrations studied. Not only is it lognormal, but the breadth of the peak remains consistent as well. This fact is confirmed by the absence of change in σ that is observed for EuTc-citrate in FIGS. 6 and 7. In contrast, the breadths of the peaks and their corresponding σ values change markedly for daunomycin and doxorubicin (FIG. 7). Furthermore, there are notable exceptions to the lognormality of the data acquired for daunomycin and doxorubicin (FIG. 1). In the case of daunomycin, there appears to be a growing population of cells on the low fluorescence side of the peak as the extracellular concentration increases. Conversely, doxorubicin's small departure from lognormality occurs at low extracellular drug concentrations. These changes occur in concert with changes in the slope of the drug uptake versus concentration of the drug in the extracellular medium, as emphasized by the dashed versus solid lines in FIGS. 3B and 3C. The net MFI of intracellular EuTc-citrate is strongly correlated with both extracellular citrate concentration and intracellular $^{210}$Po activity (FIG. 3A), indicating that MFI of EuTc-citrate is related to $^{210}$Po toxicity.

Similarly, the data for daunomycin and doxorubicin in FIGS. 3B-C support the notion that the extent of agent incorporation by cells can be used as a predictor of their cytotoxicity. To validate the latter, cell survival is plotted against net MFI and extracellular drug concentration, or against intracellular $^{210}$Po activity and absorbed dose to the cell nucleus from $^{210}$Po-citrate (FIG. 4A). For $^{210}$Po-citrate, less than 2-logs of cell killing is observed. The relationship between the surviving fraction and net MFI (or cellular activity or absorbed dose) is exponential. Notably, neither the slope of the cellular uptake curve (FIG. 3A), nor the slope of the survival curve (FIG. 4A), nor the value of the shape parameter (FIGS. 6 and 7), change over the course of the concentrations required to achieve zero to two logs of cell kill. These conditions may be requirements needed to achieve a monoexponential survival curve and avert tailing of the survival curve. The data in FIGS. 4B-C illustrate that cell survival is related to extracellular concentration (or net MFI) of daunomycin and doxorubicin by a 2-component exponential function, with tails analogous to those observed using radiochemicals.

Daunomycin and doxorubicin are closely related anthracyclines and interact with DNA by intercalation. Based on extracellular drug concentration in V79 cell cultures, daunomycin ultimately emerged to be more cytotoxic than doxorubicin. While this may be due to differences in the extent to which the drugs are incorporated, this cannot be ascertained by flow cytometry alone but rather with the help of cellular uptake studies with daunomycin and doxorubicin labeled with $^3$H or $^{14}$C at known specific activities. What is certain is that the slope of the cellular uptake curves (FIGS. 3B-C), and the slope of the survival curves (FIGS. 4B-C), and the value of the shape parameter (FIG. 7), all changed over the span of concentrations required to see the emergence of a tail in the survival curves. The presence of these conditions appears to be related to the two-component exponential survival curves. In fact, the concentration (ca. 1-2 μmol/L) at which these parameters begin to change (FIGS. 2, 3, 6 and 7) appears to coincide with the transition to the second component (FIG. 4).

The mean lethal concentrations for daunomycin and doxorubicin are 0.24 and 1.26 μmol/L, respectively. This indicates that low extracellular concentrations of daunomycin are ~5× more lethal than doxorubicin in V79 cells. The mean lethal absorbed dose for $^{210}$Po-citrate is 1.2 Gy. This arises from an uptake of 0.21 mBq/cell which corresponds to about 3600 atoms of $^{210}$Po. Although the survival curve is similar to that obtained previously, the present mean lethal dose is higher than the former value of 0.7 Gy. This is largely due to improved S values. Although, there is an interest in using multimodal approaches that involve the concomitant delivery of chemotherapeutic and radiotherapeutic agents for cancer treatment, the efforts have mostly not been directed at using agent-specific distribution profiles to target all malignant cells.

To facilitate the design of cocktails that effectively target all cells of interest, an in-depth knowledge of the distribution profile of each agent is required. This warrants the ability to express cellular incorporation of agents in absolute units on a cell-by-cell basis. As an initial step towards this end, the flow cytometric histograms presented in FIG. 2 were fitted to the lognormal probability density function, and the derived shape parameters (σ) were plotted against intracellular $^{210}$Po activity or extracellular drug concentration. It is not surprising that these data are closely analogous to the established relationship between heterogeneity of intracellular incorporation of doxorubicin and extracellular drug concentration, as the shape parameter is a measure of the broadness of a distribution profile. While a small σ implies a narrow distribution profile (i.e. σ→0) when all cells incorporate the same amount of agent), a large σ signifies a wide spread in distribution. In practice, σ>0 and therefore subpopulations of cells will always incorporate subtoxic amounts of any given agent. However, as it has been shown as part of the present invention, the value of σ is not itself necessarily the primary determinant of the shape of the survival curve. Rather, changes in the value of σ (FIG. 7) and changes in the slope of the cellular uptake curves (FIGS. 3B and 3C), appear to correlate with changes in the transition from the first component to second component of the two-component exponential survival curves (FIGS. 4B and 4C). Hence, formulation of recipes for combined modality therapy should seek to use flow cytometry distribution information to identify the drug concentration that will achieve the first component of killing.

A similarly optimized additional agent could then be added with the aim of targeting cells that had low uptake of the first drug. Successively adding additional drugs would ultimately seek to achieve a net heterogeneity of σ→0, based on incorporation of all agents. It should be noted that findings related to the distribution of therapeutic agents among a population of cells, and their corresponding dose response characteristics, may vary considerably depending on cell type and the microenviroment within which the cells reside. In addition, factors such as resistant subpopulations can have a significant impact on the shape of the response curve. Therefore, caution is needed when cocktails are formulated based on in vitro findings and then extrapolated to the in vivo setting encountered in the clinic.

The present invention demonstrates that the distribution of cellular radioactivity within a cell population is adequately described by a lognormal probability density function. The ubiquitousness of the lognormal distribution has been further demonstrated by the cellular uptake profiles of two different chemotherapeutic drugs. Changes in the value of the lognormal shape parameter and changes in the slope of the cellular uptake curves with increasing drug concentration flag the onset of saturation in the dose response curve. Accordingly, measurement of these changes using flow cytometry, or another analytical technique, preferably a high-speed technique, can be employed to rapidly predict biological response to the drug, and ultimately to formulate a highly effective therapeutic cocktail.

Cocktails of Therapeutic Agents

One multiple-therapeutic agent embodiment of the present invention involves a cocktail of radioimmunotherapy and chemotherapy agents. Informed radioimmunotherapy/chemotherapy is one option for front-line defense against metastatic and residual disease in adjuvant external beam radiotherapy and surgery. However, one major limitation has been the difficulty in relating cellular incorporation of therapeutic agents, on a cell-by-cell basis, to resulting biological effects. The models for predicting the distribution of cytotoxic agents among a cell population, at the single-cell level, as disclosed above, now also provide a cocktail approach whereby all malignant cells can be effectively targeted. This flow cytometry-based approach, taking explicit account of the lognormal distribution of cellular uptake of the agents, enables prediction of treatment response on a cell-by-cell basis, and has now been shown to be invaluable in the selection of agents for the design of highly effective therapeutic cocktails that are capable of targeting the diversity in tumor cell populations. Further, such cocktails can be created not only for treatment of cancer, but also for infectious diseases, and other diseases that are amenable to targeted therapies. Furthermore, this single-cell Monte Carlo technique can be used to resolve difficulties encountered when attempting to predict biological response at the multicellular level using macroscopic mean agent doses.

Over the past two decades, interest in the use of α-emitting radionuclides in radioimmunotherapy has grown significantly. However, a major unresolved concern is that the toxicity of α-emitting radionuclides does not allow administration of high activities. As such, targeting procedures would need to be optimized to minimize normal tissue toxicity. This can be achieved via multi-modality radioimmunotherapy, which employs combinations of radioimmunotherapy and chemotherapy. Multi-modality radioimmunotherapy approaches seek not only to effectively target all malignant cells, but also to significantly reduce the amount of each constituent of the cocktail. To guide design of effective cocktails of α-emitting radiopharmaceuticals and chemotherapy drugs, there is the need to assess the role of non-uniform agent distribution on modification of α-particle radiotoxicity by chemotherapy drugs. Furthermore, the capacity to predict such modifications in treatment response on a cell-by-cell basis should greatly improve treatment outcomes through individualized staging prior to therapy.

As has now been demonstrated, concomitant treatment of Chinese hamster V79 cells with an α-emitting radiochemical, $^{210}$Po-citrate, and either daunomycin or doxorubicin, resulted in an enhancement of α-particle radiotoxicity. Further, the toxicity of the combination treatment can be predicted with a Monte Carlo simulation approach based only on knowledge of the initial slope of the cell survival curves of the individual agents and information on the distribution of agent incorporation among cell populations.

EXAMPLES

Example 1

Predicting Cell Survival Based on Flow Cytometry Gating

Three approaches to modeling the surviving fraction of cells were undertaken. In the first approach, flow-cytometry fluorescence histograms of agent uptake were prepared and the cells were gated relative to control autofluorescence using FlowJo® software (TreeStar). The fractions of agent-negative cells were defined as the proportions of fluorescence spectra that had intensities below the maximum intensities of control samples (i.e. the fraction of fluorescence spectra below maximum autofluorescence). For $^{210}$Po, 0.1 mM citrate which corresponded to a nontoxic cellular activity of 0.03 mBq/cell was used for autofluorescence. In this simple approach, the gated subpopulations of agent-negative cells were considered as survivors, whereas gated subpopulations of agent-positive cells were considered dead. The surviving fraction was taken as the number of agent-negative divided by the sum of agent-negative and agent-positive cells.

Figure 5A:
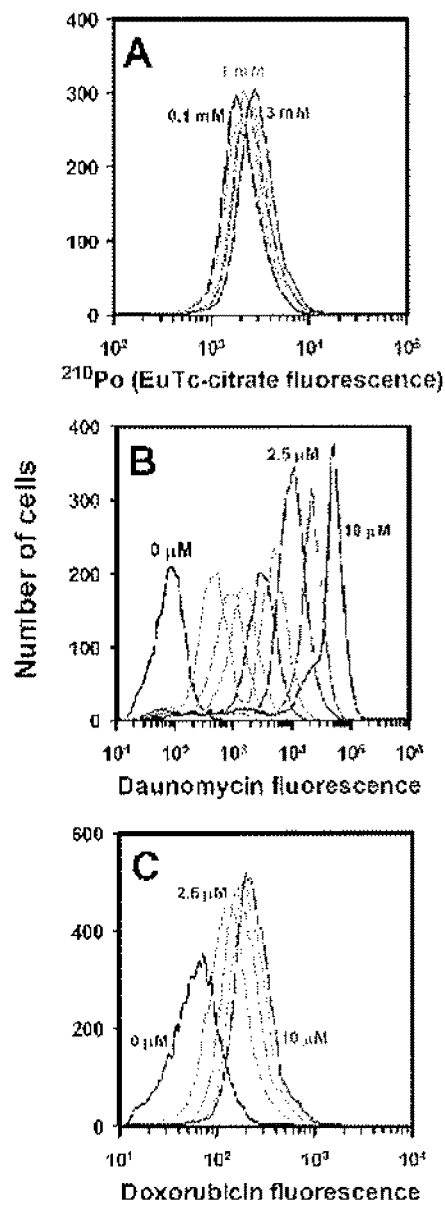
FIGS. 5A and 5B shows a flow chart of the Monte Carlo procedure for determining fraction of surviving cells based on cellular fluorescence intensity profiles of the incorporated agent.
Figure 5B:
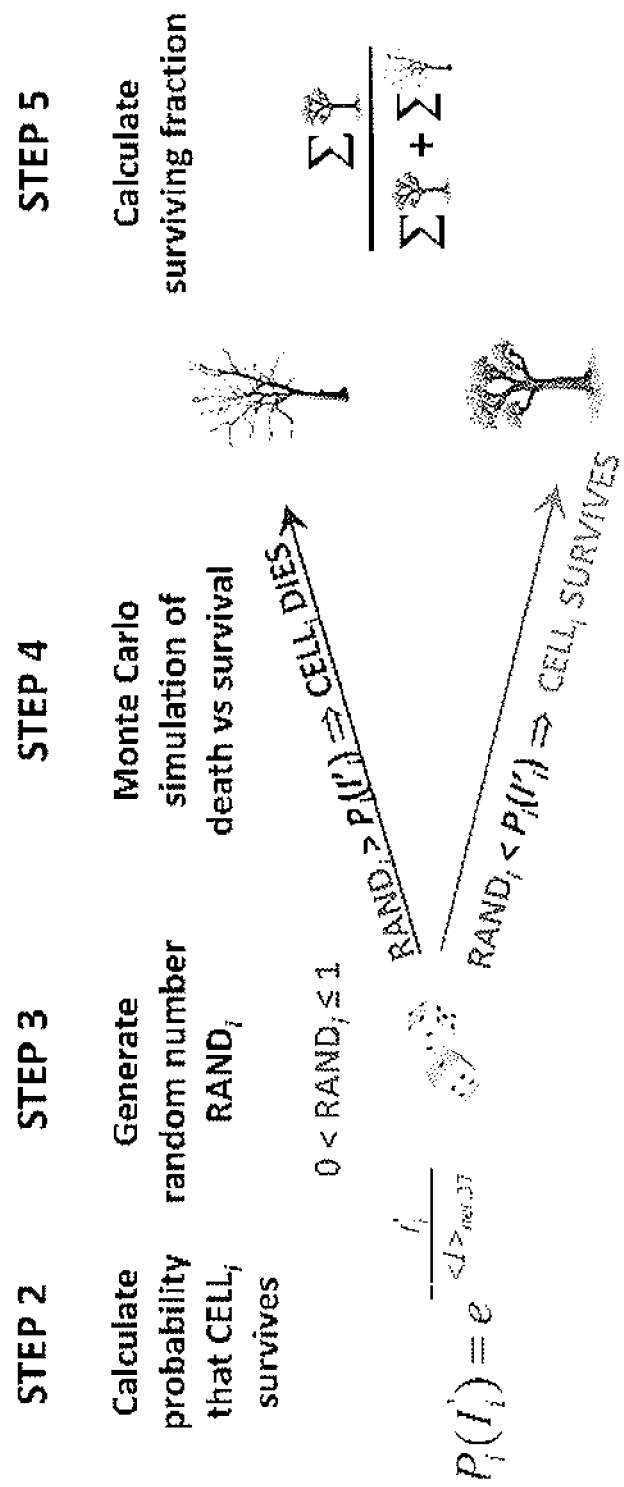

Predicting Cell Survival Based on Monte Carlo Analysis of Cellular Fluorescence Intensity The second approach, depicted in FIG. 5, employs a Monte Carlo simulation that uses experimental individual cell fluorescence intensities $I_i$ for the agent under consideration. The flow cytometry data for citrate, daunomycin, and doxorubicin, consisting of fluorescence intensities emitted by individual cells in a population after incorporation of a fluorescent agent ($I_1, I_2, I_3, \ldots, I_i$), were exported into Microsoft Excel (Redmond, Wash.) spreadsheets. These raw values were normalized to $\langle I \rangle_{net}$ as per Equation (2).

$$I'_i = I_i \left( \frac{\langle I \rangle_{net}}{\langle I \rangle} \right), \tag{2}$$

where $$\langle I \rangle = \frac{1}{N} \sum_{i=1}^{N} I_i,$$

and N is the number of cells analyzed. The cytotoxicity of a therapeutic agent in a given cell is assumed to be exponentially related to the cellular uptake of the agent. Exponential functions are widely used to model the probability of cell death following cytotoxic insults from ionizing radiation and chemicals. Accordingly, the survival probability $P_i$ of the $i^{th}$ cell with normalized fluorescence intensity, $I'_i$, may be expressed as:

$$P_i(I'_i) = e^{-\frac{I'_i}{\langle I \rangle_{net,37}}}. \tag{3}$$

The resulting probability for each cell was compared with a random number generated from a uniform probability distribution by Excel, $0 < RAND_i \leq 1$, and a binary value was assigned to the survival $s_i$ of the $i^{th}$ cell:

$$s_i = \begin{cases} 0 & \text{dead cell} \quad RAND_i > P_i(I'_i) \\ 1 & \text{live cell} \quad RAND_i \leq P_i(I'_i) \end{cases} \quad (4)$$

A new random number was generated for each cell. This type of random number approach to determining the fate of each cell was also used in our recent communication (Rajon et al. 2011). Therefore, the surviving fraction of a population of N cells treated with a given concentration of an agent that yields net mean fluorescence intensity per cell, $<I>_{net}$, may be expressed as:

$$SF(\langle I \rangle_{net}) = \frac{1}{N}\left(\sum_{i=1}^{N} s_i\right) \quad (5)$$

Care must be exercised when $$\sum_{i=1}^{N} s_i$$

is small because the statistical uncertainty of the Monte Carlo calculation of SF is high under such circumstances. This occurs at high agent concentrations that cause low surviving fractions. This is best circumvented by analyzing a larger number of cells. A less preferable alternative is to run additional simulations with new random number sequences and average the results.

Predicting Cell Survival Based on Mean Cellular Uptake

The third approach uses the same Monte Carlo approach for determining the fate of each cell, however, it is assumed that every cell in the population contains the same amount of drug. That is, each cell is assigned a fixed net mean fluorescence $<I>_{net}$ which in essence corresponds to case wherein the lognormal shape parameter $\sigma \to 0$. In this instance, the probability of survival of the $i^{th}$ cell is given by $$P_i(\langle I \rangle_{net}) = e^{-\frac{\langle I \rangle_{net}}{\langle I \rangle_{net,37}}}. \quad (6)$$

The surviving fraction of the population is obtained using the same Monte Carlo method described above except that Equation (6) was used instead of Equation (3) to calculate the probability of survival.

Materials and Methods

Cell Line and Monolayer Culture

Chinese hamster V79 lung fibroblasts were used. Two different formulations of minimum essential media (MEMA and MEMB) were used, as known in the literature. All media and supplements were Gibco (Carlsbad, Calif.), including fetal calf serum (catalog no. 10437, lot no. 539574). For routine maintenance, cells were grown as monolayers in Falcon 25-cm² tissue culture flasks (BD, Franklin Lakes, N.J., catalog no. 353082) at 37° C., 5% $CO_2$-95% air, and subcultured twice weekly. For experiments, V79 cells (passage 4-11) were transferred into Falcon 225-cm² flasks (BD, catalog no. 353138), and were used upon reaching 80%-90% confluence.

Suspension Cell Culture

Cells grown in 225-cm² flasks were trypsinized (0.25% trypsin, Gibco, catalog no. 25200-056), and MEMB was added to obtain $2 \times 10^6$ cells/mL. Aliquots of 1 mL were placed in Falcon 17×100 mm polypropylene tubes (BD, catalog no. 352018) and placed on a rocker-roller (Thermo Fisher, Fair Lawn, N.J.) for 3 hours at 37° C. with 5% $CO_2$ and 95% air. After this conditioning period, cells were treated with drug or radiochemical. Cell cultures were exposed to radiochemical and drugs for 0.5 and 2.5 h, respectively.

Cellular Incorporation of $^{210}$Po-Citrate, Daunomycin, and Doxorubicin $^{210}$Po-Citrate. The uptake of $^{210}$Po-citrate was determined on a cell-by-cell basis by flow cytometric techniques, using $^{210}$Po-free citrate. Briefly, V79 cells ($2 \times 10^6$ cells/mL) were treated with 0-3 mmol/L of citrate and incubated on a rocker-roller as described earlier. Cellular uptake of citrate was tracked using an europium tetracycline (EuTc) conjugate. Samples were washed 2× with 10 mmol/L MOPS buffer (Sigma, St. Louis, catalog no. M3183), after a 30 min exposure to citrate. The cells were resuspended in 1 mL of MOPS buffer containing EuTc (Sigma, catalog nos. 203254 for Eu and T7660 for Tc), transferred into 7 ml polystyrene flow cytometry tubes (BD, catalog no. 352054), and were incubated at room temperature (~22° C.) in the dark for 30 min. The final concentration of EuTc was 100 µmol/L. EuTc forms a ternary complex with citrate (EuTc-citrate) which is excitable at 488 nm, and its emission can be captured within the wavelengths transmitted by the 610/20 filter. After washing 2× with MOPS buffer, the samples were resuspended in 1 mL of MOPS buffer, passed 5× through a 21-gauge needle, and were analyzed by flow cytometry using an LSR II flow cytometer (BD), equipped with a 488 nm laser. Cellular incorporation of citrate, expressed in terms of the fluorescence intensity per cell or mean fluorescence intensity (MFI) of EuTc-citrate, was used as a surrogate measure cellular uptake of $^{210}$Po-citrate.

Daunomycin and Doxorubicin.

To determine the cellular uptake of daunomycin and doxorubicin, the cells were treated with 0-10 µmol/L of each drug in MEMB and incubated on a rocker-roller for 2.5 h. The cells were washed 2× with phosphate buffered saline (PBS), resuspended in 1 mL of PBS, passed 5× through a needle, and were immediately subjected to flow cytometric analysis. The 488 nm laser was used to excite intracellular daunomycin and doxorubicin, and the emission spectra were captured within the wavelengths transmitted by the 575/26 and 530/30 filters, respectively. Cellular incorporation of drugs was also expressed as MFI.

Toxicity of $^{210}$Po-Citrate $^{210}$PoCl$_4$ in 2 mol/L HCl was obtained at 370 MBq/mL from Eckert & Ziegler Isotope Products (Valencia, Calif., catalog no. 6310). $^{210}$Po-citrate was prepared as follows. Briefly, PoCl$_4$ solution was mixed with 1 mol/L sodium citrate in the ratio of 1:7 (final pH 5.8), and was diluted with MEMB to a volume of 4 mL (final pH 6.9). One milliliter of MEMB containing $^{210}$Po-citrate was added to the 1 mL of conditioned V79 cultures ($2 \times 10^6$ cells/mL), to arrive at a concentration of 0-250 kBq/mL (pH 6.9-7.0). After incubating for 30 min, the cells were washed 2× with MEMB, resuspended in 2 mL of MEMB, and incubated on a rocker-roller for 2.5 h to simulate concomitant drug exposure. The cells were resuspended in a 5 mL of MEMB, passed 5× through a needle, and counted with a Beckman Coulter Model Z2 (Brea, Calif.). Aliquots (500 µL) of the cell suspension were transferred to vials, mixed with 5 mL Ecolume (MP Biomedical, Solon, Ohio, catalog no. 882470), and counted with a Beckman Coulter LS6500, and the mean activity per cell was determined (efficiency, 50% as per prior studies). Aliquots of about $5 \times 10^5$ cells were counted in triplicate for $^{210}$Po activity and the cpm ranged from $10^3$-$10^5$. The triplicate measurements kept statistical variations to a minimum. Each sample was serially diluted and plated in Falcon 60×15 mm tissue culture dishes for colony formation. Cultures were incubated for 7 days, and the colonies were fixed in 95% ethanol, stained with 0.01% Amido Black, washed in tap-water, air-dried, and counted.

Biologic Clearance of $^{210}$Po

To determine the biologic clearance of $^{210}$Po from the cells, $4 \times 10^6$ cells/mL were treated with $^{210}$Pocitrate as described above. After two washes with MEMB, the cells were resuspended in 5 mL of MEMB, passed 5× through a needle, and Coulter counted. Aliquots of 500 μL of cells were transferred to vials and mixed with Ecolume. The remaining cell suspension was plated into 25-cm² flasks (1.0, 0.5, 0.5, 0.2 and $0.2 \times 10^6$ cells/flask). The cultures were harvested after 24, 48, 72, and 96 h, respectively. Each sample was processed for cell counting and liquid scintillation counting as described. All vials were counted after the last harvest. The ratio of cellular activity at each time point to that immediately after treatment was calculated and plotted.

Toxicity of Daunomycin and Doxorubicin

After conditioning, the cell cultures were treated with daunomycin (Sigma, catalog no. D8809) or doxorubicin (Sigma, catalog no. 44583) to a final concentration of 0-10 μmol/L in MEMB. The tubes were returned to the rocker-roller for 2.5 h. The cells were then processed for colony formation as described above.

Analysis of the Flow Cytometry Data for Cocktails of Agents

Samples.

Flow cytometry control samples consisted of cells treated with the following agents: 1) untreated, 2) 3 mM citrate, 3) 0.63 μM daunomycin, and 4) 2.50 μM doxorubicin, Daunomycin+citrate test samples were 0.63 μM daunomycin+0.1, 0.2, 0.5, 1.0, 1.5, 2.0, 2.5, or 3.0 mM citrate. Doxorubicin+citrate test samples were 2.50 μM doxorubicin+0.1, 0.2, 0.5, 1.0, 1.5, 2.0, 2.5, or 3.0 mM citrate.

Acquisition.

Fluorescence intensity histograms were acquired for each sample using an LSR II flow cytometer (BD). The europium tetracycline-citrate complex, daunomycin, and doxorubicin were excited with a 488 nm laser, and their emission spectra were captured within the wavelengths transmitted by the 610/20, 575/26 and 530/30 filters, respectively.

Analysis.

FlowJo software (TreeStar) was used to analyze each sample. Dot plots of forward scatter versus side scatter were created to gate cells from debris. Fluorescence intensities were compensated for overlapping emission spectra.

Results

Predicting Cell Survival Based on Flow Cytometry Gating

Cells with fluorescence intensities greater than the maximum autofluorescence were considered as agent-positive, while those with lower intensities were agent-negative. For $^{210}$Po-citrate and doxorubicin, most cells emerged as agent-negative regardless of agent concentration. This occurred because of the relatively small increase in <I> with increasing extracellular concentration of the agent. The proportion of daunomycin-positive cells consistently increased with increasing drug concentration. Conversely, the proportion of daunomycin-negative cells decreased substantially with increasing drug concentration. When surviving fraction, defined in this instance as fraction of agent-negative cells, was plotted as a function of agent concentration, it was apparent that agent-negativity, based on what might be considered conventional flow-cytometry gating, is not necessarily indicative of the ability of a cell to survive. For $^{210}$Po and doxorubicin, the fraction of agent-negative cells was found to significantly overestimate cell survival over the entire range of agent concentrations assessed. While there was relatively good agreement between daunomycin-negativity and clonogenic cell survival at low concentrations, the fraction of cells that were apparently drug negative failed to accurately predict survival at higher drug concentrations.

Predicting Cell Survival Based on Monte Carlo Analysis of Cellular Fluorescence Intensity To assess the capacity of Monte Carlo simulation of cell death and survival from cellular fluorescence data acquired by flow cytometry, the procedure depicted in FIG. 5 was employed. Only the net mean lethal fluorescence intensity, $<I>_{net,37}$ and the measured fluorescence intensity in each cell of the treated population were needed to theoretically model the surviving fraction following treatment by each drug. Panels A, B and C of FIG. 5 show the lognormal nature of the distribution of measured fluorescence intensities following treatment with graded concentrations each drug. Application of Equation (3) to the two cell populations provides the survival probabilities $P_i(I'_i)$ of each cell in populations treated with 0 or 5 μM daunomycin. By generating a random number $RAND_i$ between 0 and 1 (FIG. 5, STEP 3), and comparing it with the survival probability $P_i(I'_i)$, the fate ($s_i$) of each cell was determined according to Equation (4) (FIG. 5, STEP 4). The surviving fraction of cells, $SF(<I>_{net})$, based on normalized individual fluorescence intensities $I'_i$, were then calculated using Equation (5) (FIG. 5, STEP 5). There is a transition from nearly all live cells to nearly all dead cells as the agent concentration is increased.

The process described above for determining the surviving fraction $SF(<I>_{net})$ was carried out for each of the cell populations which were treated with 0.1-3 mM citrate. The resulting theoretically modeled surviving fractions $SF(<I>_{net})$ are plotted in FIG. 6A for $^{210}$P-citrate, along with the experimental clonogenic survival data. This process was repeated for daunomycin and doxorubicin to create the theoretical data points in FIGS. 6B and 6C, respectively. The Monte Carlo simulated cell survival is in good agreement with colony forming ability of V79 cells after treatment with the cytotoxic agents.

Predicting Cell Survival Based on Mean Cellular Uptake

Survival curves based on Monte Carlo analysis wherein each cell in the population contains the same amount of drug are presented as straight, dashed lines in FIG. 6. These provide an important point of comparison with the flow cytometry gating model and the Monte Carlo model that accounts for the lognormal distribution of cellular uptake of the agent.

Prediction of Multiple Agent Toxicity

The approach for modeling cell survival using a Monte Carlo simulation is based on individual cell fluorescence intensities $I_i$ for a single agent as described above. When cells were concomitantly treated with multiple agents, the fluorescence intensities of all agents within each cell of each treated population were measured simultaneously using flow cytometry. These data were used to perform a Monte Carlo analysis to simulate the surviving fraction of cells after treatment with all possible combinations of the agents. This process is depicted for a cocktail of to agents in FIG. 8.

Flow cytometry of a population of N cells treated with a cocktail of agents provided the fluorescence intensity of each agent in each cell. These data were exported into Microsoft Excel (Redmond, Wash.) spreadsheets. The raw fluorescence intensities for the $j^{th}$ agent in the $i^{th}$ cell, were normalized to $\langle I_j \rangle_{net}$ for each agent as per Equation (2A)

$$I'_{ij} = I_{ij}\left(\frac{\langle I_j \rangle_{net}}{\langle I_j \rangle}\right), \quad (2A)$$

where $$\langle I_j \rangle = \frac{1}{N}\sum_{i=1}^{N} I_{ij},$$

and $\langle I_j \rangle_{net}$ denotes the net mean fluorescence intensity per cell following exposure to the $j^{th}$ agent. $\langle I_j \rangle_{net}$ is determined by subtracting the mean control autofluorescence, $\langle I_j \rangle_{control}$, from the mean fluorescence intensity per cell in a treated population as defined by Equation (1A):

$$\langle I_j \rangle_{net} = \langle I_j \rangle - \langle I_j \rangle_{control} \quad (1A)$$

For $^{210}$Po-citrate, a citrate concentration of 0.1 mM, which was found to correspond to a nonlethal cellular activity of 0.03 mBq/cell, was used for control autofluorescence. The net mean cellular fluorescence intensity of Agent j that yields 37% survival is denoted $\langle I_j \rangle_{net,37}$ [20]. To account for natural variations in $\langle I_j \rangle_{net,37}$ from experiment to experiment, it is necessary to obtain an $\langle I' \rangle_{37}$ for each experiment from a calibration of an experimentally determined surviving fraction. Assuming that the toxicity of the $j^{th}$ agent in a given cell population is exponentially related to the cellular uptake of the agent, the surviving fraction of such a population based on its net mean fluorescence intensity, $\langle I'_j \rangle$, is:

$$SF_j = e^{-\frac{\langle I'_j \rangle}{\langle I'_j \rangle_{37}}} \quad (7)$$

For instance, using the net mean fluorescence intensity of a cell population corresponding to 10% cell survival, $$\langle I'_j \rangle_{37} = \frac{\langle I'_j \rangle}{\ell n(0.1)}.$$

At the single-cell level, the survival probability of the $i^{th}$ cell with normalized fluorescence intensity, $I'_{ij}$ may be expressed as (FIG. 8, STEP 2):

$$P_i(I'_{i1}) = e^{-\frac{I'_{ij}}{\langle I'_j \rangle_{37}}} \quad (6A)$$

Therefore, the survival probabilities for the $i^{th}$ cell when treated with Agent 1 or Agent 2 are given by $$P_i(I'_{i1}) = e^{-\frac{I'_{i1}}{\langle I'_1 \rangle_{37}}} \text{ and } P_i(I'_{i2}) = e^{-\frac{I'_{i2}}{\langle I'_2 \rangle_{37}}},$$

respectively.

To model cell survival following treatment with a cocktail of two agents, we hypothesize that a cell may die due to Agents 1 and 2 working independently or interactively. The survival probability $P_i(I'_{i1}, I'_{i2})$ of the $i^{th}$ cell is represented by:

$$P_i(I'_{i1}, I'_{i2}) = \Omega(I'_{i1}, I'_{i2})P_i(I'_{i1})P_i(I'_{i2}) \quad (8)$$

$$\Omega(I'_{i1}, I'_{i2}) = \begin{cases} 1 & \text{agents work independently} \\ P_i(I'_{i1})P_i(I'_{i2}) & \text{agents work interactively} \end{cases} \quad (8A)$$

where $\Omega_i(I'_{i1}, I'_{i2})$ is a term that accounts for the interaction of the two agents.

The probability calculated with Equations (8) and (8A) was then compared with a random number, $0 < RAND_i \leq 1$ (FIG. 8, STEP 3), and a binary value was assigned to the survival $s_i$ of the $i^{th}$ cell:

$$s_i = \begin{cases} 0 & \text{dead cell} \quad RAND_i > P_i(I'_{i1}, I'_{i2}) \\ 1 & \text{live cell} \quad RAND_i \leq P_i(I'_{i1}, I'_{i2}) \end{cases} \quad (4A)$$

A new random number was generated for each cell. This approach to determining the fate of each cell (FIG. 8, STEP 4) was also used in our recent communications. Therefore, the surviving fraction of a population of N cells treated with Agent 1+Agent 2 is given by (FIG. 8, STEP 5):

$$SF_i(I'_{i1}, I'_{i2}) = \frac{1}{N}\left(\sum_{i=1}^{N} s_i\right) \quad (5A)$$

One embodiment of the invention employs a Monte Carlo approach to simulate the fate of each cell based on its experimentally determined drug uptake and used this information to calculate a surviving fraction for the entire cell population. The resulting surviving fractions were compared to experimentally determined values. Two different methods of predicting cell survival following a toxic insult were considered. The first approach addressed the role of individual agent uptake (i.e. cell fluorescence) in cell survival. The fate of individual cells can be determined based on their incorporation of a given agent, in this case daunomycin. However, it is worth noting that the magnitude of a cell's survival probability, per se, is not conclusive as to whether a cell survives or dies. Hence, there is a need to simulate the fate of each cell within the population using Monte Carlo techniques.

In FIG. 6, experimentally determined cell survival data are compared with theoretical cell survival data that were simulated by Monte Carlo analysis. However, before applying the Monte Carlo approach to account for the experimental lognormal uptake distributions, it is instructive to first see how this model behaves when each cell is assumed to contain the same uptake (i.e. the mean uptake). As expected, when theoretical survival is simulated assuming that each cell in the population contains an agent quantity corresponding to the net mean cellular fluorescence intensity, the resulting survival curve is monoexponential (FIG. 6, dashed lines). In this approach, the fact that each cell in the population is assumed to incorporate the same amount of agent implies σ→0. The data clearly show that, regardless of the agent, the theoretical survival derived from mean cellular fluorescence can recapitulate clonogenic survival only within the first exponential component of cell kill.

Figure 6B:
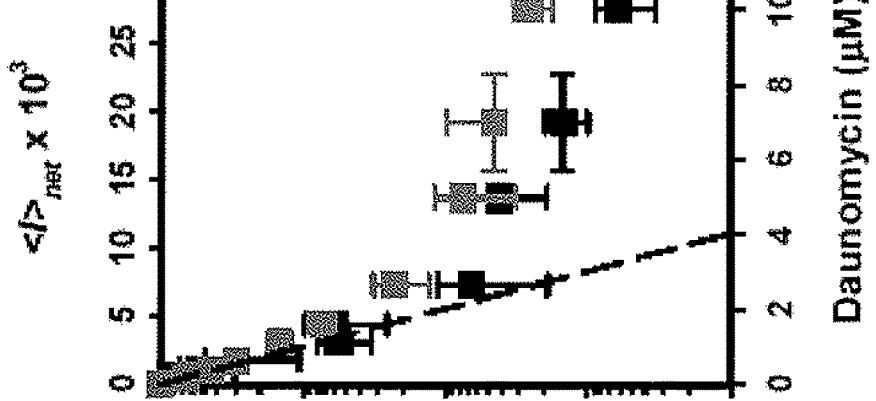
Figure 6C:
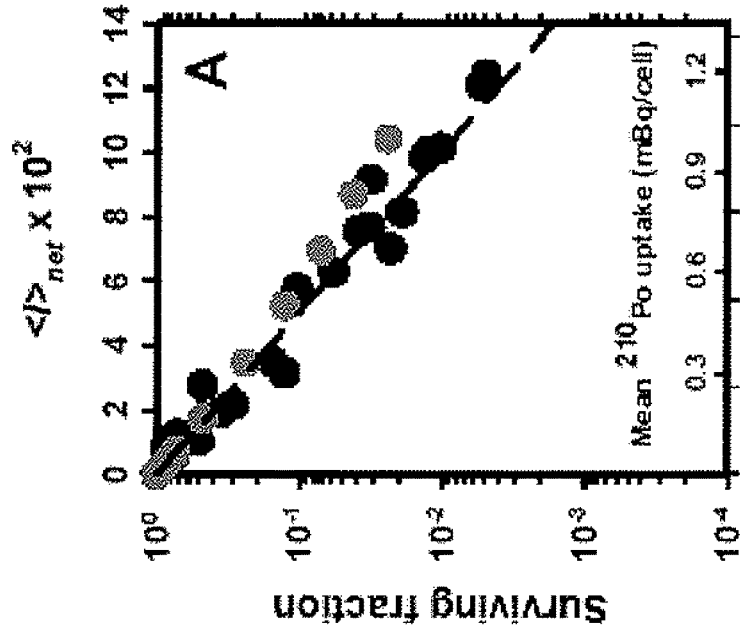
Figure 7A:
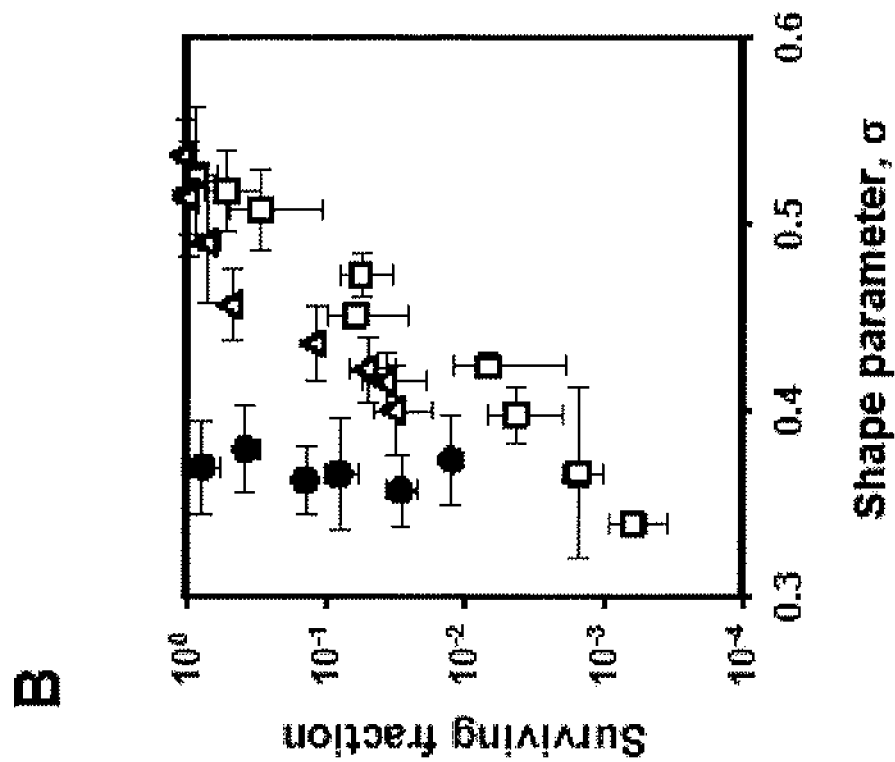
FIG. 7A displays the lognormal shape parameters σ for $^{210}$Po-citrate, daunomycin, and doxorubicin plotted against intracellular $^{210}$Po activity (●, solid line), and extracellular concentration of daunomycin (□, dashed line) and doxorubicin (Δ, dotted line), respectively.
Figure 7B:
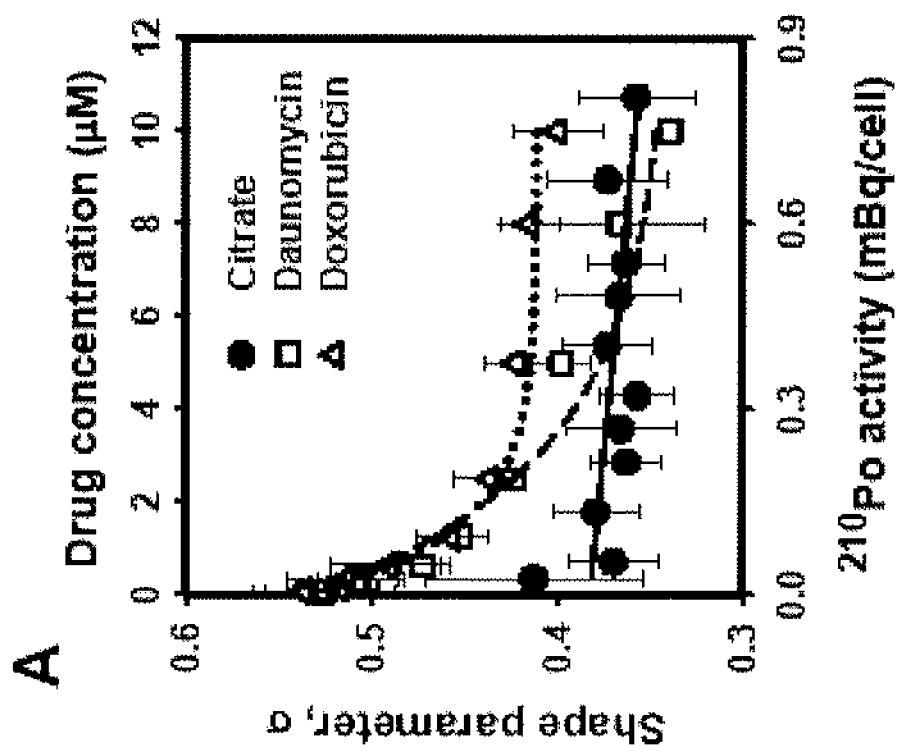
FIG. 7B displays the surviving fraction versus shape parameter for $^{210}$Po-citrate (●), daunomycin (□), and doxorubicin (Δ). Error bars represent SE of three independent experiments.

In contrast to the poor match between experimental data and the mean approach, Monte Carlo simulation of cell survival in a manner that accounts for the lognormal uptake distribution provides a very good prediction of clonogenic survival following treatment with $^{210}$Po-citrate, daunomycin, and doxorubicin (FIG. 6). Moreover, this model accurately predicts the transition between the first and second components of cell killing. This transition coincides with that observed when the lognormal shape parameter is plotted as a function of drug concentration. It should be noted that in the case of daunomycin, the Monte Carlo approach accurately predicts cell survival at low drug concentrations within the first log of cell kill but there is some deviation from experimental values at high drug concentrations (FIG. 6B). Nevertheless, the fit is remarkably good compared with the more conventional approach based on mean drug uptake (FIG. 6, dashed lines). Approaches based on mean uptake adequately predict the response in the low-dose realm, but fail to predict the upward trend in the survival curve that arises as a consequence of the lognormal distribution of drug uptake.

Toxicity of Cocktails

To evaluate cytotoxicity of combined treatment of V79 cells with $^{210}$Po-citrate and daunomycin, or $^{210}$Po-citrate and doxorubicin, the surviving fraction of clonogens was plotted as a function of mean cellular uptake of $^{210}$Po (FIG. 9) and as a function of mean absorbed dose to the cell nucleus. When cells were only treated with $^{210}$Po-citrate, the survival curve can be described by a 1-component exponential function. When cells were concomitantly treated with a single drug concentration and varying amounts of $^{210}$Po-citrate, the dose-response curves followed a 2-component exponential function. The data corresponding to the combined treatments were then corrected for drug toxicity, by dividing the surviving fraction for each datum point by the surviving fraction for drug alone (SF=0.10), and replotted in FIG. 9. Both of the corrected cell survival curves emerged below those obtained for $^{210}$Po-citrate alone. This indicates that daunomycin and doxorubicin enhance the radiotoxicity of α-particles in V79 cells. As illustrated in FIG. 9A, the enhancement of α-particle radiotoxicity by daunomycin was independent of radiation absorbed dose beyond about 0.5 Gy (~0.09 mBq/cell). On the other hand, the increased kill provided by doxorubicin showed a dose-dependent increase (FIG. 9B).

Figure 8A:
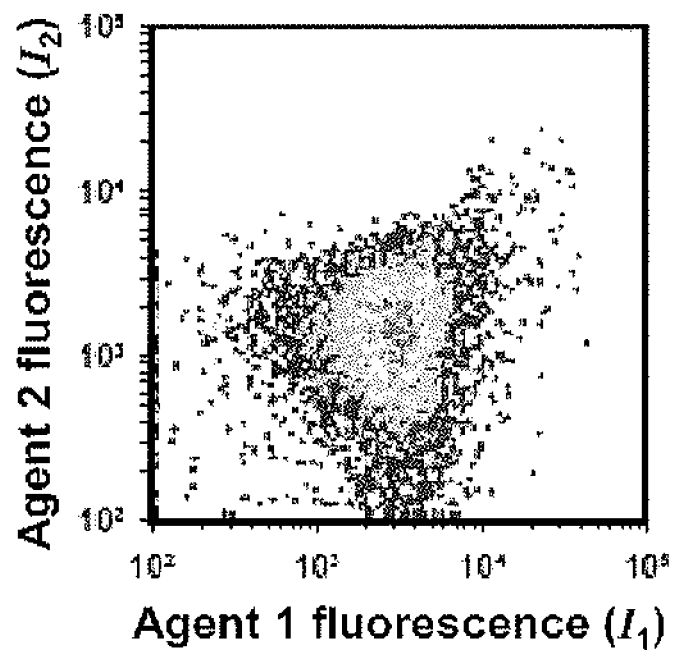
FIGS. 8A and 8B shows a flow chart of the Monte Carlo procedure for determining fraction of surviving cells based on cellular fluorescence intensity distributions that arise after treatment of cells with a cocktail of two therapy agents (Agent 1 and Agent 2).
Figure 8B:
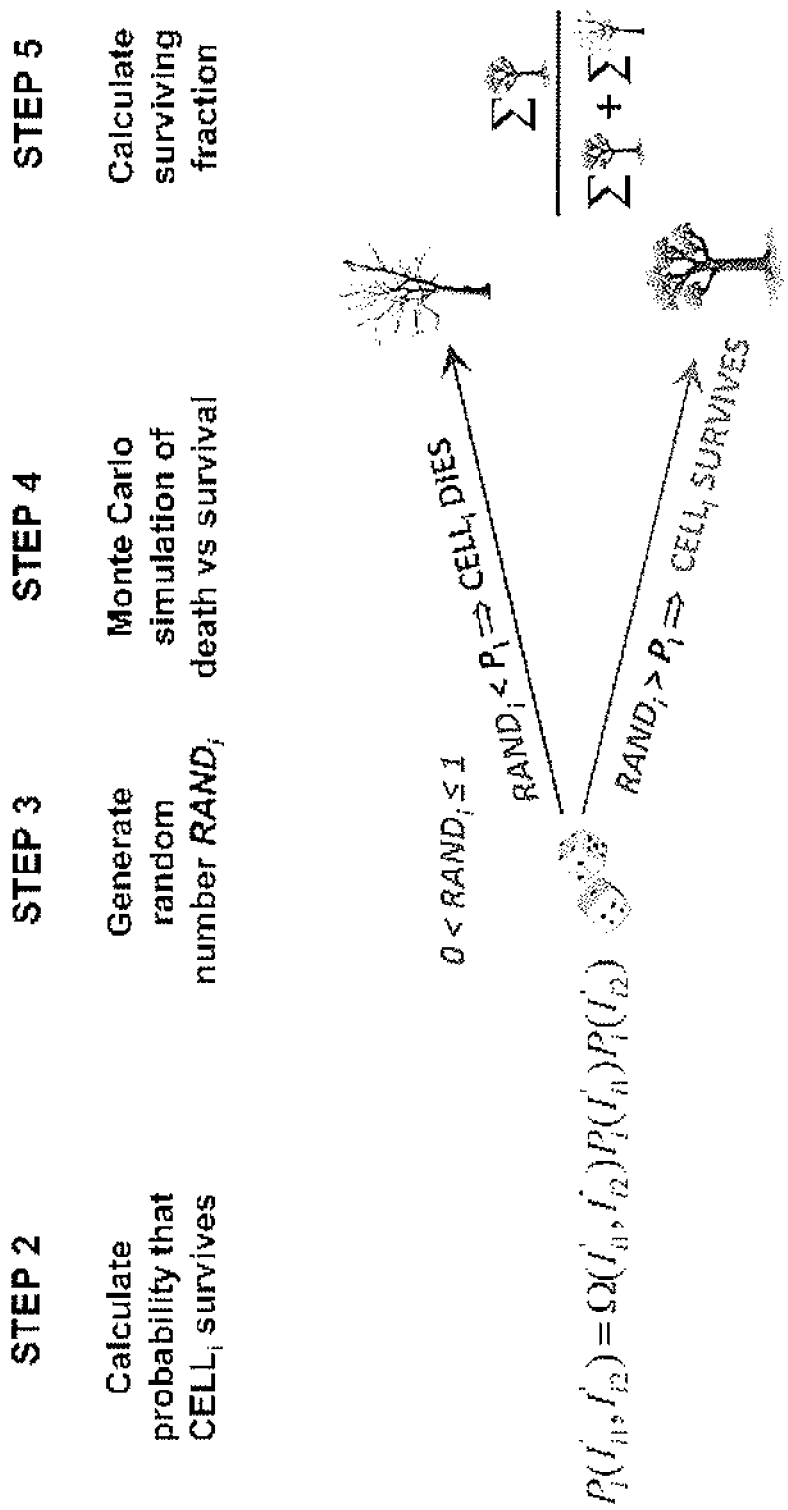

Predicting Cell Survival Based on Monte Carlo Analysis of Cellular Fluorescence Intensity The procedure depicted in FIG. 8 was used to assess the capacity of flow-cytometry assisted Monte Carlo simulation to recapitulate cell death and survival after exposure to $^{210}$Po-citrate+daunomycin or $^{210}$Po-citrate+doxorubicin. Following STEPS 2-4 of FIG. 8, application of Equations (6A), (8), (8A) and (4A) yields a plot of live and dead cells for fixed daunomycin concentration and varying concentrations of $^{210}$Po-citrate. The surviving fraction of a given cell population, based on normalized individual fluorescence intensities, $I'_{ij}$, was then calculated using Equation (5A) (FIG. 8, STEP 5). The symbols in FIG. 10 represent the theoretically modeled surviving fractions for $^{210}$P-citrate+daunomycin and $^{210}$P-citrate+doxorubicin. The theoretical data are superimposed on curves representing least squares fits to the experimental clonogenic survival data that were shown in FIG. 9. The open symbols were obtained assuming independent action of the agents (upper form of Equation (8A)), while closed symbols represent modeled cell survival when the agents are considered to interact (lower form of Equation (8A)). The Monte Carlo simulation that implemented agent-interaction is in excellent agreement with the experimental data.

These data provide experimental evidence that treatment of Chinese hamster V79 cells with a cocktail of $^{210}$Po-citrate and a chemotherapy drug (daunomycin or doxorubicin) causes cytotoxicity greater than expected based on the lethality of the agents when used alone (FIG. 9). These data show that when the effect of each chemotherapy drug is corrected for, the corrected survival curves do not coincide with that for the $^{210}$Po alone treatment. The curves emerge below the $^{210}$Po survival curve. This is indicative of a chemical enhancement of α-particle radiotoxicity, or perhaps that cells that are not adequately labeled with $^{210}$Po-citrate (e.g. low end of the lognormal uptake distribution) are killed by the chemotherapy drug. The flow-cytometry assisted Monte Carlo simulation of cell survival can distinguish these possibilities.

In the cocktail embodiment, the flow cytometry-assisted Monte Carlo model has been applied to agent-incorporation data obtained after treating cells with a cocktail of $^{210}$Po-citrate+daunomycin or $^{210}$Po-citrate+doxorubicin. The test of the capacity of this approach to predict the cytotoxicity of a combination therapy is presented in FIG. 10 where experimentally determined cell survival curves (solid curves) are compared with theoretical cell survival as simulated by Monte Carlo analysis (symbols). When it is assumed that the agents act independently, the model fails to predict clonogenic cell survival (FIG. 10, open symbols). However, when the agents are assumed to interact, the Monte Carlo simulation predicts cell survival exquisitely at all intracellular activities of $^{210}$Po (FIG. 10, closed symbols). This suggests that, at the levels of cell kill observed, the chemotherapy agents provide a chemical enhancement of the α-particle radiotoxicity in V79 cells rather than killing cells that are inadequately labeled with $^{210}$Po-citrate. The latter possibility may become important at very high levels of cell kill (i.e. 5 or 6 logs of kill).

The cocktail approach accurately predicts the experimental toxicity of the $^{210}$Po-citrate+daunomycin/doxorubicin cocktails based only on knowledge of the initial slope of the dose-response curves for each agent (i.e. $<I_j>_{37,net}$) and the cellular uptake distribution of the ingredients of the cocktail. This can be extremely helpful in designing more effective cocktails for targeted therapy; these cocktails may consist of a sizeable number of agents.

Although the use of α-emitting radionuclides in radioimmunotherapy has gained considerable interest, the relatively high potency of α-particles limits the amount of activity that can be administered. To benefit from the potency of α-particles and yet maintain low normal tissue toxicity, the use of low doses of cocktails of α-particle based radioimmunotherapeutics and chemotherapy drugs that effectively target all malignant cells is warranted. Yet, only one study has been reported to demonstrate enhancement of the anti-tumor effects of α-particles in a mouse tumor model by paclitaxel. While the exact mechanism of that enhancement is not known, it was suggested to be dependent on the sequence of the administration of the therapeutic agents, and was both angiogenic and apoptotic by nature. Predicting response to radionuclide therapy and chemotherapy drugs on a cell-by-cell basis enables the dissecting of mechanisms involved with drug interaction, and thereby improves the design of more effective cocktails for targeted therapy. Therefore, it is possible that agents previously discarded on the basis of single-agent toxicity may become key ingredients in a cocktail by virtue of their capacity to target a few cells that only incorporate small amounts of the primary drug.

Of particular importance in the above-described embodiments is the fact that the flow-cytometry assisted Monte Carlo simulation of cell survival requires knowledge of only the initial slope of the dose-response curve (i.e. $<I>_{net,37}$) and the uptake distribution of the radiopharmaceutical or drug. With these two pieces of information, the entire clonogenic survival curve can be recapitulated including both the 1- or 2-component exponential shapes. The approach applies equally well for drugs that are not likely to be characterized by a lognormal uptake distribution such as Hoechst 33342, whose uptake is directly proportional to DNA content.

Special attention should be given to the process of normalizing the fluorescence data obtained by flow cytometry. The measured fluorescence intensities are dependent on flow cytometry hardware (e.g. laser wavelength and intensity), settings (e.g. amplification), etc. Given that the fluorescence intensity is ultimately related to drug uptake in terms of quantities such as mass (g) and/or activity (Bq), there will be a need to implement calibrations for these quantities. The mean activity per cell can be readily measured with high accuracy and precision using standard radiation detection devices. This information, along with the distribution of cellular fluorescence intensities, provides detailed knowledge of the activity in each cell of the population. Furthermore, calibration with drugs with known specific activity (Bq/g) can provide detailed knowledge of the mass of drug in each cell of the population. Accordingly, survival probabilities might be represented by $$P_i = e^{-\frac{m_i}{\langle m \rangle 37}} \text{ and } e^{-\frac{a_i}{\langle a \rangle 37}},$$

respectively, where the mass of drug in the cell, $m_i = \xi I'_i$ and/or the amount of radioactivity in the cell $a_i = \kappa I'_i$. The constants $\xi$ and $\kappa$ represent the slopes of plots of $<m>$ and $<a>$ versus $<I>_{net}$, respectively. These probabilities would be independent of flow cytometry hardware and instrument settings.

Not specifically addressed are the underlying reasons why the experimental and Monte Carlo derived clonogenic survival curves deviate most from those for an average concentration of agent at the higher concentrations. Although not wishing to be bound by any theory, in the realm of chemotherapy, this is often ascribed to resistant subpopulations that may express high levels of the multidrug resistant protein MDR1. One function of this protein is to facilitate the active removal of toxins from the cell, thereby foiling its therapeutic intent. Low cellular uptake by some cells within a population is also especially important for receptor-targeted agents such as radiolabeled antibodies used for radioimmunotherapy. The number of receptors on a given cell can vary widely over a cell population such that sublethal activity may be taken up by a subpopulation. The flow cytometry assisted Monte Carlo embodiment described above can be extremely useful in modeling the consequence of such non-uniformities, thereby reducing the level of experimental effort that is needed to optimize a therapy. Furthermore, a variety of other capabilities can be built into the model to account for other toxic insults to the cell population such as cross-dose received from radiations emitted by neighboring cells, and radiation- or chemically-induced bystander effects.

The use of flow cytometry to predict clonogenic survival using either agent-negative subpopulations of cells or flow cytometry-assisted Monte Carlo simulation has been demonstrated in the present disclosure. Generally, the fraction of apparently agent-negative cells cannot predict cell survival as determined by colony forming ability. However, it has been demonstrated that Monte Carlo simulation using cellular agent incorporation based on individual cell fluorescence intensity of therapeutic agents is a suitable predictor of cell survival. This flow cytometry based approach, which takes explicit account of the lognormal distribution of cellular uptake of the agents, offers a rapid means for determining treatment response on a cell-by-cell basis, and is invaluable in the selection of agents for the design of highly effective therapeutic cocktails that are capable of targeting the diversity in tumor cell populations. Such cocktails can be created not only for treatment of cancer, but also for infectious diseases and other diseases that may be amenable to targeted therapies. Furthermore, the single-cell Monte Carlo embodiment can be used to resolve difficulties encountered when attempting to predict biological response at the multicellular level using macroscopic mean agent doses.

Example 2

This example illustrates the Monte Carlo methods described herein to increase the effectiveness of RIT by formulating cocktails of radiolabeled antibodies. Three monoclonal antibodies (Ab) were pre-labeled with fluorochromes, and breast cancer cells were treated with graded concentrations. Optimal concentrations were determined by flow cytometry and Monte Carlo analysis according to the method of U.S. Pat. No. 8,874,380. Cells were treated with Ab cocktails and it was found that the overall distribution of Ab binding was changed, resulting in a predicted increase in killing of the tumor cell population.

Materials and Methods

Cell Culture

Cell culture protocol was according to the methods set forth above. Briefly, MDA-MB-231-luc-D3H1 (MDA-MB-231) human breast cancer cells were grown in minimum essential medium (MEM). The media contained 10% fetal calf serum, 2 mM L-glutamine, 100 units/ml penicillin, 100 µg/ml streptomycin, 10 mg/ml non-essential amino acids. Cells were grown as monolayers in 75-cm² flasks and were used for experiments (passages 13-19) at 70-90% confluence.

Antibody Labeling

Cells were trypsinized (0.5% Trypsin/EDTA), resuspended in complete growth media, syringed using a 21 gauge needle, counted, and then centrifuged for 5 min. Cells were then resuspended in growth media containing only penicillin-streptomycin (incubation media) and 3 ml containing 0.5×10⁶ cells was placed in 5 ml round bottom tubes. All tubes were centrifuged for 5 min. The cells were then resuspended in 100 µl antibody solution, the concentration of which depended on the specific treatment represented by a given tube. Biolegend Pacific Blue anti-EpCAM (9C4) and APC anti-EGFR, and Santa Cruz PE anti-Tag-72 were used. The tubes were then placed on a hematology mixer for 2 hours at 37° C., 5% $CO_2$, 95% air. After the labeling, 3.0 ml of incubation medium was placed into each tube to facilitate pellet formation, and the tubes were centrifuged for 5 min. Cells were resuspended in 1.0 ml of PBS and analyzed using a BD LSR II Flow Cytometer.

Analysis

The fluorescence intensity of a cell is directly proportional to the amount of bound antibody. Further, it was assumed that the cellular uptake of a hypothetical radionuclide is proportional to the uptake of the antibody. With these assumptions, the Monte Carlo simulation disclosed herein was utilized to predict the surviving fraction of the cells (on the cellular level) for each antibody concentration for each experiment. Graphs of antibody concentration versus surviving fraction and the lognormal shape parameter of antibody distribution were used to determine the optimal concentration of each antibody for each cell line. It has been shown that the inflection point of a concentration versus lognormal shape parameter graph can be used to predict the inflection point of a concentration versus surviving fraction graph. This principle applied to all of the experiments for which the shape parameter changed. A modified Monte Carlo simulation was applied to the combined antibody treatments.

Results

Fluorescence histograms from the initial experiment for each antibody were examined. The anti-EGFR histograms became taller and thinner with increasing antibody concentration. The anti-EpCAM treatment histograms differed little in shape from one another. The anti-Tag-72 histograms had a main peak that stayed in the same place for all of the treatments, but with increasing antibody concentration had a second peak develop that became wider and taller. The changes in shape were quantified by plotting the lognormal shape parameter as a function of antibody concentration. The lognormal shape parameter for a given antibody concentration is indicative of the width of the distribution of antibody among the cells. The shape parameter for the anti-EpCAM did not change as a function of antibody concentration. The predicted survival curves were plotted for each "radiolabeled" antibody. The inflection point of the shape parameter versus concentration graph matched up with the inflection point of the survival curve for anti-EGFR and anti-Tag-72. Based upon the survival curves and shape parameter graphs, the optimal concentration for all three antibodies was 1.0 μg/ml for the MDA-MB-231 cell line.

Figure 17A:
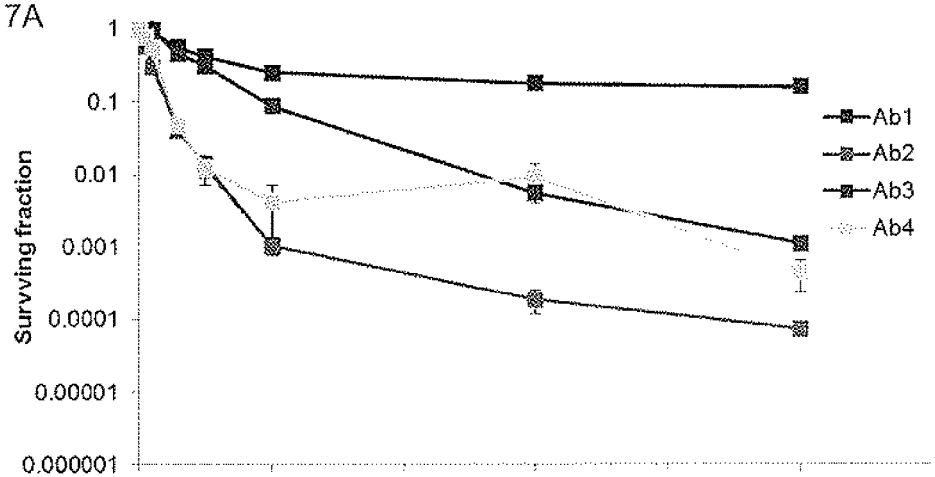
FIGS. 17A, 17B and 17C shows mean surviving fraction of MDA-MB-231 cells as function of antibody concentration for different combinations of $^{211}$At-labeled antibodies (specific activity, 4.25×10$^{15}$ Bq/mol), highlighting effect of single antibodies (FIG. 17A), double-antibody cocktails (FIG. 17B), and triple- and quadruple-antibody cocktails (FIG. 17C). Error bars represent SEM (n=3; for Ab3, n=2).
Figure 17B:
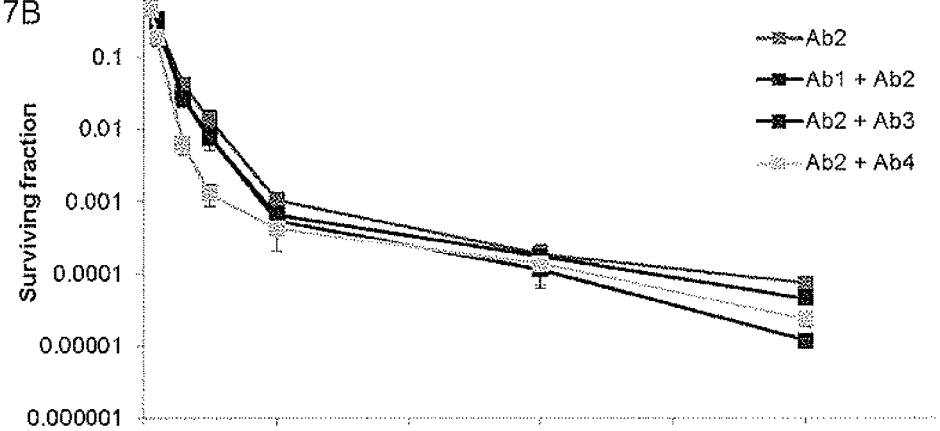
Figure 18:
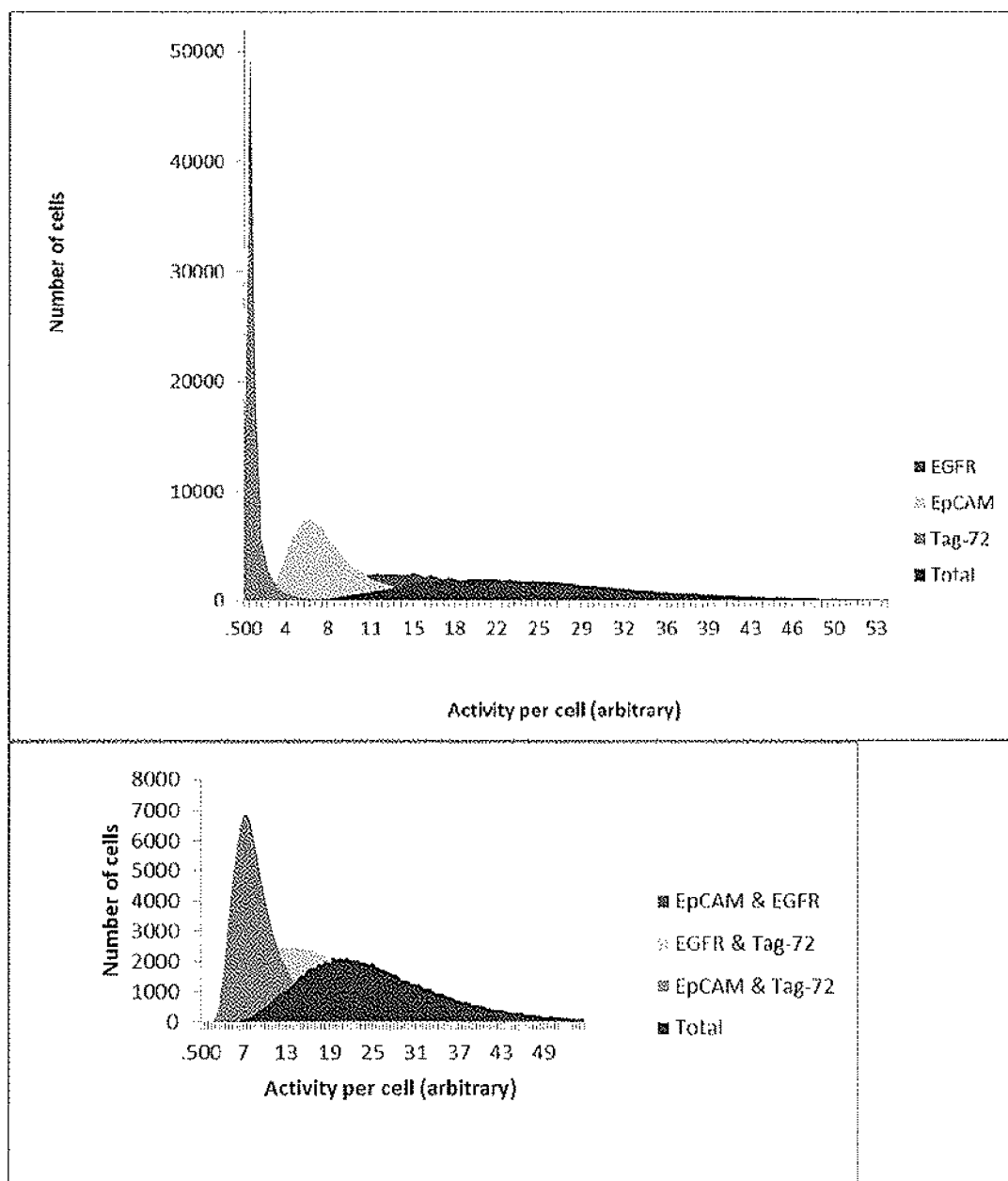
FIG. 18 shows simulated radiation dose histograms for individual antibodies and antibody pairs (inset) for the 0.1 µg/ml treatment of the antibody cocktail.
Figure 19:
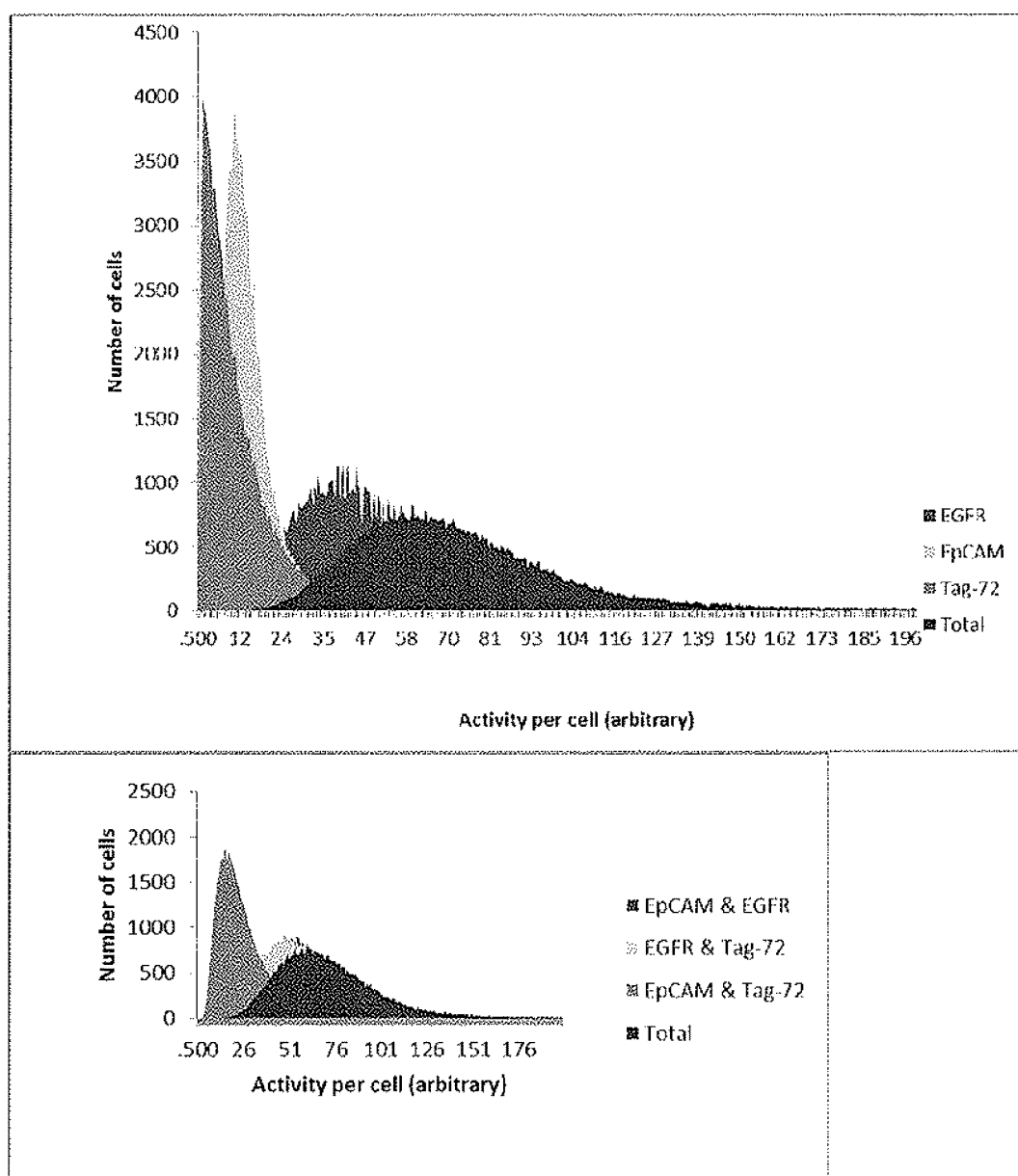
FIG. 19 shows simulated radiation dose histograms for individual antibodies and antibody pairs (inset) for the 10 µg/ml treatment of the antibody cocktail.

The survival curve for the antibody cocktail had an inflection point that occurred at about 0.5 μg/ml (FIG. 17). Survival curves corresponding to different combinations of antibodies within the cocktail reveal that anti-EGFR had the most impact on "cell death," followed by anti-EpCAM, with anti-Tag-72 only having an appreciable effect at the inflection point and when antibody concentration exceeded 3 μg/ml. Notably, the antibody cocktail raised the amount of "radioactivity" delivered to the least labeled cell by approximately 300% in the 0.1 μg/ml (pre-saturation) treatment, relative to the individual antibodies alone (FIG. 18). The cocktail also raised the minimum "radioactivity" per cell in the 0.1 μg/ml treatment relative to pairs of antibodies (FIG. 18 inset). The cocktail was observed to raise the minimum amount of "radioactivity" in the 10 μg/ml (saturation) treatment by 200% relative to individual antibodies alone (FIG. 19). Like in the 0.1 μg/ml treatment, the cocktail saw a greater delivery of radiation dose to the cells than the pairs of antibodies did in the 10 μg/ml treatment.

The increased amount of radiation dose delivered by the antibody cocktail relative to individual antibodies and antibody pairs (FIGS. 18 and 19) demonstrates the increased therapeutic effectiveness that is observed in FIG. 17. A doubling or tripling of the minimum cellular radiation dose delivered by the cocktail can translate to a substantial increase in tumor cell killing by RIT. These data provide evidence that an antibody cocktail is more efficient than individual antibodies in RIT, with respect to cell killing.

Example 3

This example illustrates a method to increase the effectiveness of RIT by formulating cocktails of radiolabeled antibodies, in which the surviving fraction of a target cell population exposed to therapeutic agents can be predicted using a flow-cytometry assisted simulation, such as a Monte Carlo simulation, without fitting the fluorescence spectra to the lognormal probability density function and then accounting for the lognormal characteristics of the distribution in the simulation. Four monoclonal antibodies (Ab) were pre-labeled with fluorochromes, and breast cancer cells were treated with graded concentrations. Optimal concentrations were determined by flow cytometry and Monte Carlo analysis. Cells were treated with Ab cocktails and it was found that the overall distribution of Ab binding was changed, resulting in a predicted increase in killing of the tumor cell population.

Materials and Methods

Cell Culture

Cell culture protocol was according to the methods set forth above. Briefly, MDA-MB-231-luc-D3H1 (MDA-MB-231) human breast cancer cells were grown in minimum essential medium. The medium was supplemented with heat-inactivated 10% fetal calf serum, 2 mM L-glutamine, 100 units of penicillin per mL, 100 μg streptomycin per mL, and 10 mg nonessential amino acids per mL. Cells were grown as monolayers in 175 cm$^2$ flasks at 37° C., 5% $CO_2$-95% air, humidified, and were used at 70-90% confluence for the following example, Antibody Selection and Labeling Cells were trypsinized (0.5% Trypsin/EDTA), re-suspended in medium, syringed using a 21 gauge needle, counted, and then centrifuged for 5 min. at 27° C. at 1040 rpm. The supernatant was removed, and cells were then re-suspended in medium containing only penicillin-streptomycin incubation medium and 3 mL aliquots containing 10$^6$ cells was placed in 5 ml round bottom tubes. All tubes were centrifuged for 5 min at 27° C. at 1040 rpm. The cells were then re-suspended in 100 μL of 1 μg/ml antibody solution medium. Biolegend APC anti-EGFR(AY13), Pacific Blue anti CD-73(AD2), PE anti CD-44(BJ18), PE anti-CD-221 (1H7), Pacific Blue anti-EpCAM(9C4), R&D Systems AF-488 anti CD-44(691534), AF-700 anti-GLUT1 (202915), Santa Cruz PE anti-EGFR(528), AF-405 anti-EGFR(R-1), PE anti-Tag-72(B72.3), and Millipore PerCP anti-EGFR(LA22) were used. The combination of each antibody in a given combination was equivalent. The tubes were shielded from light and placed in a hematology mixer for 2 hours at 37° C. in 5% $CO_2$/95% air. After labeling, the cells were washed and re-suspended in 1.0 ml of PBS. Analysis was undertaken using a LSR II flow cytometer. 300,000 cells were minimally analyzed for each sample. Apparent debris was gated out, and compensation was performed.

Determination of Number of Molecules of Each Antibody on Each Cell

The fluorescence intensity of a cell is directly proportional to the amount of bound antibody. Bangs Quantum Simply Cellular Calibration Beads were used to ascertain the number of antibodies bound to each cell using the cell's fluorescence. Cellular uptake of a hypothetical radionuclide is proportional to the uptake of the antibody. Calibrations were conducted for each color within this example, and no historical caliburations were used.

Simulation of Antibody Radiolabeling and Determination of Distribution of Cellular Absorbed Data The compensated flow cytometric fluorescence data for all cells in each sample population were copied from FlowJo and pasted into an Excel spreadsheet (Microsoft), and the number of molecules of each antibody on each cell was calculated using the calibration coefficients. Each antibody was then armed with Astatine-211, initially assuming a specific activity of $4.25 \times 10^{15}$ Bq/mol ($^{211}$At-trastuzumab, 4.4-100 kBq/μg; molecular weight, $1.6 \times 10^5$ g/mol as cited in literature) and that each antibody delivers an initial activity $A_i$ Bq to the $i^{th}$ cell that is directly proportional to the number of molecules of that antibody that is bound to the cell. Additional specific activities were studied as per Table 1 and Table 2 below. The time-integrated activity coefficient ã was assumed to be 36,180 s, the physical half-life of Astatine-211. The cellular S value was taken to be $4.14 \times 10^2$ Gy Bq$^{-1}$ s$^{-1}$, which is the absorbed dose to the cell nucleus per decay of Astatine-211 and its daughter Polonium-211 on the surface of a spheric cell with radius 5 μm and nuclear radius 3 μm. With these assumptions, the absorbed dose $D_i$ to the $i^{th}$ cell in each sample population was calculated for each antibody according to $D_i = \tilde{a} A_i S$. This resulted in a distribution of absorbed doses for each sample population. The same approach was adopted for 2 additional α-particle-emitting radionuclides, Bismuth-213 and Actinium-225. For Bismuth-213, specific activity was $1.16 \times 10^{17}$ Bq/mol, ã was 3,864 s, and S was $5.32 \times 10^{-2}$ Gy Bq$^{-1}$ s$^{-1}$. For Actinium-225, specific activity was $8.14 \times 10^{13}$ Bq/mol., a was $1.21 \times 10^6$ s, and S was $1.65 \times 10^{-1}$ Gy Bq$^{-1}$ s$^{-1}$. Daughter radionuclides were included in the cellular S values.

TABLE 1

Dependence of Relative Advantage on Specific Activity When Cells are Treated with Radiolabeled Ab2 v. Cocktail of Radiolabeled Antibodies Specific Activity →→ Increasing →→

| Relative Advantage | A | B | C |
|---|---|---|---|
| $\dfrac{SF([^{211}At]Ab2)}{SF([^{211}At]Ab2 + [^{211}At]Ab3 + [^{211}At]Ab4)}$ | 1.26 ± 0.02 | 2.67 ± 0.44 | 1.38 ± 0.62 |
| $\dfrac{SF([^{213}Bi]Ab2)}{SF([^{213}Bi]Ab2 + [^{213}Bi]Ab3 + [^{213}Bi]Ab4)}$ | 2.20 ± 0.98 | 0.65 ± 0.25 | 0.54 ± 0.15 |
| $\dfrac{SF([^{225}Ac]Ab2)}{SF([^{225}Ac]Ab2 + [^{225}Ac]Ab3 + [^{225}Ac]Ab4)}$ | 2.59 ± 0.57 | 1.53 ± 1.04 | 1.13 ± 0.75 |

For Table 1, Specific activity of $^{211}$At-antibodies is $9.25 \times 10^{13}$ Bq mol$^{-1}$ for A, $9.25 \times 10^{14}$ Bq mol$^{-1}$ for B, and $9.25 \times 10^{15}$ Bq mol$^{-1}$ for C in experiment 2 and $1.25 \times 10^{16}$ Bq mol$^{-1}$ in experiment 1. Specific activity of $^{213}$Bi-antibodies is $1.16 \times 10^{16}$ Bq mol$^{-1}$ for A, $1.16 \times 10^{17}$ Bq mol$^{-1}$ for B, and $1.56 \times 10^{17}$ Bq mol$^{-1}$ for C. Specific activity of $^{225}$Ac-antibodies is $8.14 \times 10^{12}$ Bq mol$^{-1}$ for A, $8.14 \times 10^{13}$ Bq mol$^{-1}$ for B, and $1.14 \times 10^{14}$ Bq mol$^{-1}$ for C. Ratio >1 implies cocktail is more lethal than single antibody. Ratios are average of 2 experiments. SEs are noted. Ab2 alone contains Ab2 (3 μg mL$^{-1}$), cocktail contains Ab2 (1 μg mL$^{-1}$), Ab3 (1 μg mL$^{-1}$), and Ab4 (1 μg mL$^{-1}$). Specific activity in column B is cited in literature for given radionuclide. For Actinium-225, the specific activity is reported in literature as ranging from about 1.47 MBq/mg to about 6.66 MBq/mg. For Bismuth-213, specific activity is reported in literature as ranging from about 330 MBq/mg to about 1050 MBq/mg. For Astatine-211, the specific activity is reported in literature as ranging from about 4.4 MBq/mg to about 100 MBq/mg. Column A represents 10-fold reduction of that specific activity, and column C represents specific activity required to result in about 10 survivors of analyzed population of 300,000 cells.

TABLE 2

Dependence of Relative Advantage on Specific Activity When Cells are Treated with Radiolabeled Ab4 v. Cocktail of Radiolabeled Antibodies Specific Activity →→ Increasing →→

| Relative Advantage | A | B | C |
|---|---|---|---|
| $\dfrac{SF([^{211}At]Ab4)}{SF([^{211}At]Ab4 + [^{211}At]Ab1 + [^{211}At]Ab3)}$ | 0.34 ± 0.02 | 2.83 ± 1.35 | 244 ± 69 |

TABLE 2-continued

Dependence of Relative Advantage on Specific Activity When Cells are Treated with Radiolabeled Ab4 v. Cocktail of Radiolabeled Antibodies
Specific Activity →→ Increasing →→

| Relative Advantage | A | B | C |
|---|---|---|---|
| $\dfrac{SF([^{213}Bi]Ab4)}{SF([^{213}Bi]Ab4 + [^{213}Bi]Ab1 + [^{213}Bi]Ab3)}$ | 5.10 ± 2.80 | 131 ± 88 | 230 ± 88 |
| $\dfrac{SF([^{225}Ac]Ab4)}{SF([^{225}Ac]Ab4 + [^{225}Ac]Ab1 + [^{225}Ac]Ab3)}$ | 1.62 ± 0.64 | 90.3 ± 60.9 | 167 ± 57 |

For Table 2, Specific activity of $^{211}$At-antibodies is $1.25 \times 10^{14}$ Bq mol$^{-1}$ for A, $1.25 \times 10^{15}$ Bq mol$^{-1}$ for B, and $1.25 \times 10^{16}$ Bq mol$^{-1}$ for C in experiment 2 and $5.25 \times 10^{16}$ Bq mol$^{-1}$ for experiment 1. Specific activity of $^{213}$Bi-antibodies is $1.16 \times 10^{16}$ Bq mol$^{-1}$ for A, $1.16 \times 10^{17}$ Bq mol$^{-1}$ for B, and $4.16 \times 10^{17}$ Bq mol$^{-1}$ for C in experiment 1 and $1.56 \times 10^{17}$ Bq mol$^{-1}$ in experiment 2. Specific activity of $^{225}$Ac-antibodies is $8.14 \times 10^{12}$ Bq mol$^{-1}$ for A, $8.14 \times 10^{13}$ Bq mol$^{-1}$ for B, and $4.14 \times 10^{14}$ Bq mol$^{-1}$ for C in experiment 1 and $1.14 \times 10^{14}$ Bq mol$^{-1}$ in experiment 2. Ratio >1 implies cocktail is more lethal than single antibody. Ratios are average of 2 experiments. SEs are noted. Ab4 alone contains Ab4 (3 μg mL$^{-1}$), cocktail contains Ab4 (1 μg mL$^{-1}$), Ab1 (1 μg mL$^{-1}$), and Ab3 (1 μg mL$^{-1}$ Specific activity in column B is cited in literature for given radionuclide. For Actinium-225, the specific activity is reported in literature as ranging from about 1.47 MBq/mg to about 6.66 MBq/mg. For Bismuth-213, specific activity is reported in literature as ranging from about 330 MBq/mg to about 1050 MBq/mg. For Astatine-211, the specific activity is reported in literature as ranging from about 4.4 MBq/mg to about 100 MBq/mg. Column A represents 10-fold reduction of that specific activity, and column C represents specific activity required to result in about 10 survivors of analyzed population of 300,000 cells.

Monte Carlo Modeling of Surviving Fraction (SF) of Breast Cancer Cells

The Monte Carlo simulation described herein, modified to account for specific activity and absorbed dose was utilized to predict the surviving fraction of the cells for each antibody treatment for each experiment, assuming a mean lethal dose $D_{37}$ of 1 Gy. This approach therefore calculates the probability that a given cell survives based on the absorbed dose contributions from each radiolabeled antibody on that particular cell and then uses a Monte Carlo approach to determine whether the cell lives or dies. Simulations were also conducted for all possible combinations of antibody treatments to determine the surviving faction of cells in each case. Surviving fraction was calculated in two ways: one that used the antibody uptakes for each cell as measured by flow cytometry and one in which every cell in the population is assumed to contain the same amount of antibody, which corresponds to the mean antibody uptake of the population. To study the impact of specific activity on the relative advantage of using cocktails of antibodies versus single antibodies, simulations were conducted with progressively increasing specific activities of α-emitter-labeled antibodies until only about 10 cells survived. This arbitrary point was selected to avert the difficulties in identifying the specific activity that drives the stochastic result to zero survivors.

Results

Preliminary flow cytometric analyses were performed for the candidate monoclonal antibodies to determine their relative fluorescence intensity profiles after treating MDA-MB-231 cells. Antibodies that demonstrated relatively low binding (based on their fluorescence intensity profiles) were excluded from further study. On the basis of these findings, an antibody cocktail of 4 fluorescence-labeled antibodies (Ab1-Ab4) was prepared:
  Ab1=APC anti-EGFR (AY13)
  Ab2=AF-488 anti-CD-44 (691534)
  Ab3=Pacific Blue anti-CD-73 (AD2)
  Ab4=PE anti-CD-44 (BJ18)

Figure 11:
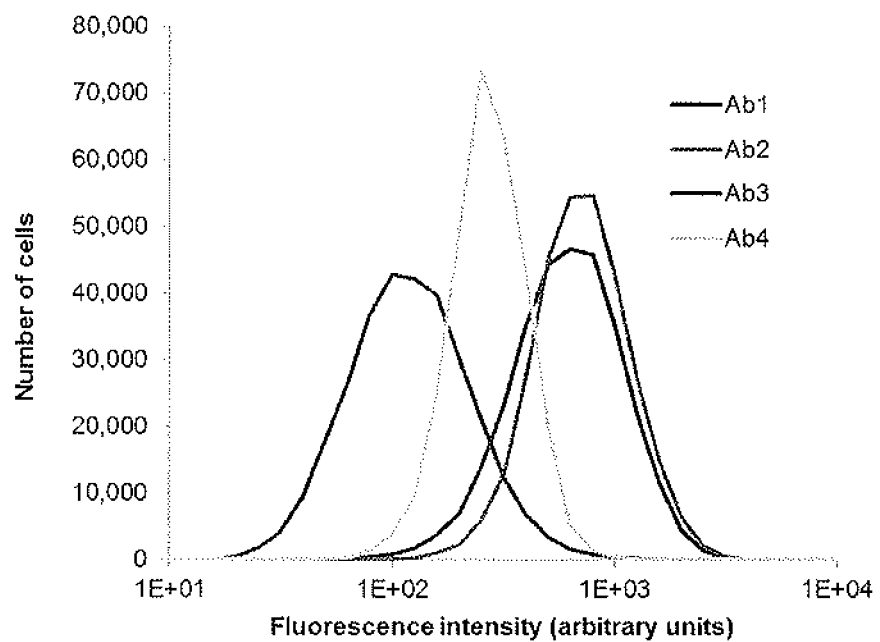
FIG. 11 shows fluorescence histograms showing distribution of uptake of Ab1, Ab2, Ab3, and Ab4 by MDA-MB-231 cells. Cells were labeled with cocktail of these 4 antibodies, concentration of each being 1 µg/mL. Data represent a combination of 3 experiments with the exception of Ab3 (2 experiments). All labeling concentrations were 1 µg/ml.
Figure 12:
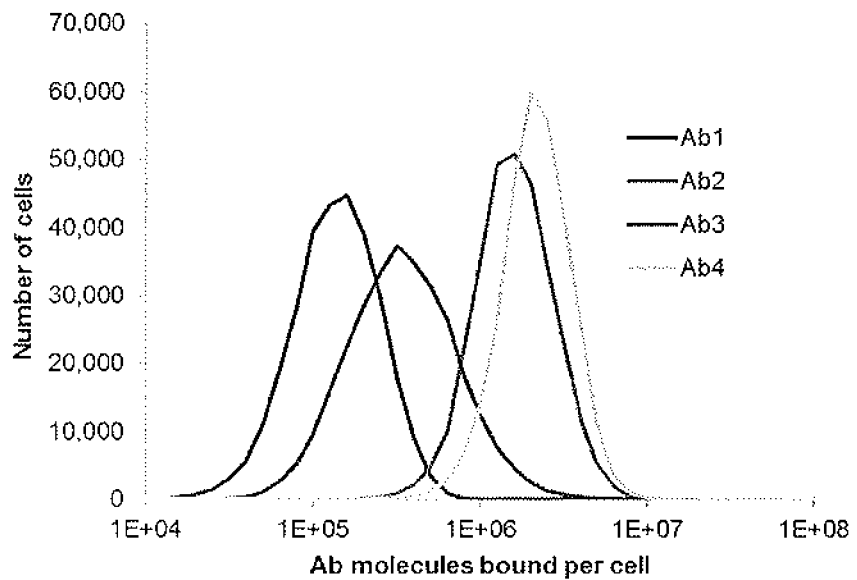
FIG. 12 shows histograms depicting distribution of number of molecules of Ab1, Ab2, Ab3, and Ab4 bound to MDA-MB-231 cells. Cells were labeled with cocktail of these 4 antibodies, concentration of each being 1 µg/mL. Data represent combination of 3 experiments with exception of Ab3 (2 experiments). Molecules per cell were determined from fluorescence intensity values based on calibrations with Quantum Simply Cellular beads.
Figure 13A:
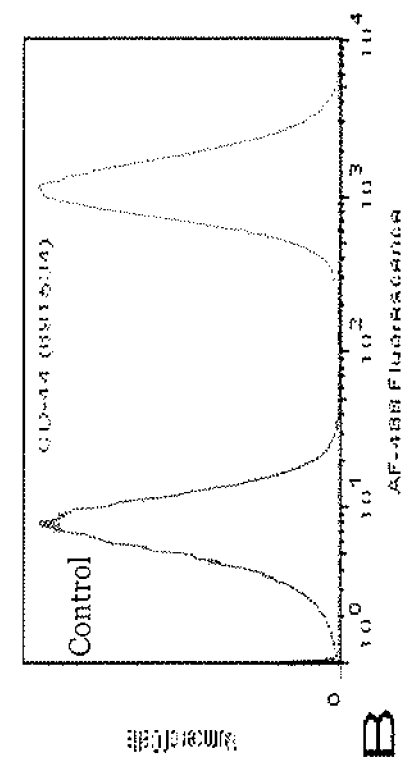
FIGS. 13A, 13B, 13C and 13D shows distribution of uptake of antibodies that target different epitopes of EGFR and CD-44, respectively.
Figure 13B:
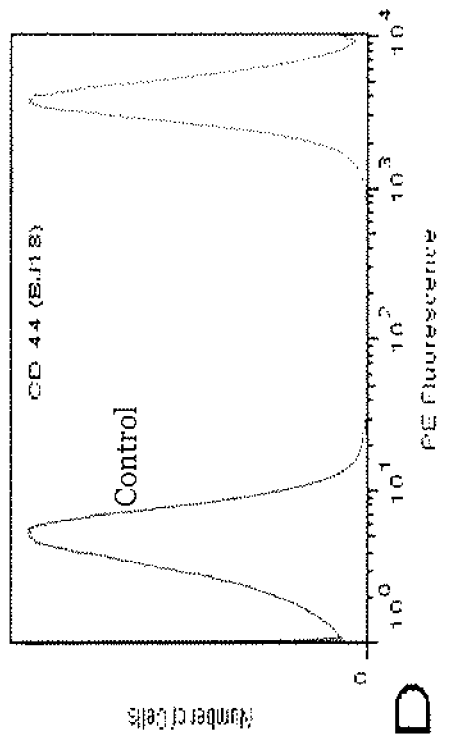
Figure 13C:
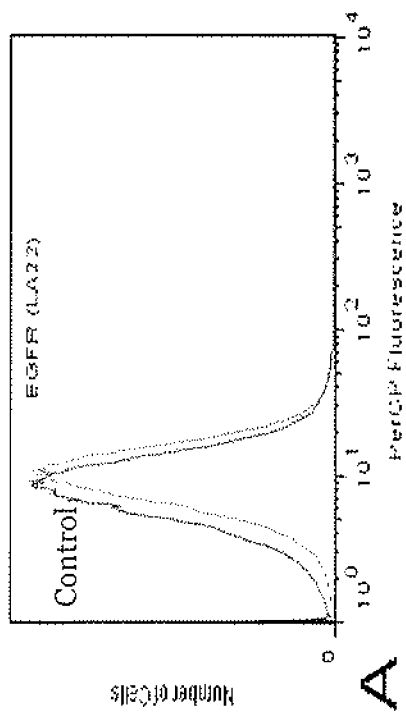
Figure 13D:
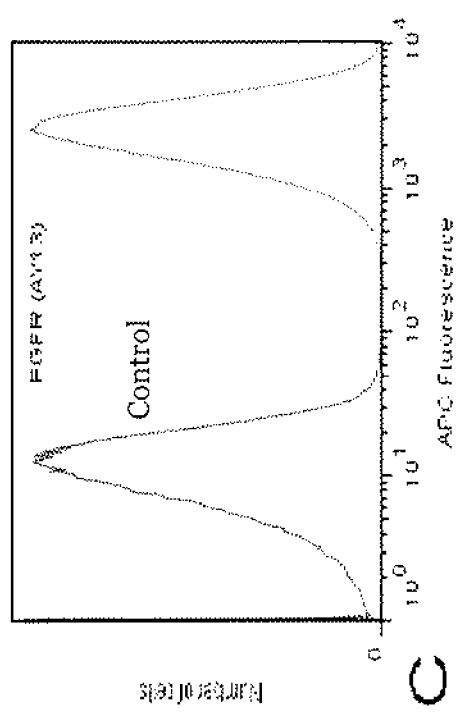

Ab2 and Ab4 target different epitopes of CD-44; preliminary studies showed that their binding was additive. Fluorescence histograms corresponding to binding of the 4 individual antibodies to MDA-MB-231 cells after treatment with an antibody cocktail containing 1 μg/mL each of Ab1, Ab2, Ab3, and Ab4 are shown in FIG. 11. The uptake of each antibody resembles a lognormal distribution. Although cellular binding of a given antibody is directly proportional to fluorescence, the relative fluorescence values between the different fluorochromes of the 4 antibodies did not reflect the relative number of antibodies bound to the cells. This was solved with Bangs calibration beads. FIG. 12 shows the distribution of each antibody on the cells, following calibration. The two epitopes of anti-CD-44 were additive, such that double the antibody was bound to cells when both epitopes were included as opposed to only a single epitope. Combining different epitopes of the same antibody was met with mixed results (FIG. 13). The cells did not appreciably express the LA22 epitope of EGFR (FIG. 13A), but expression of the AY13 epitope of EGFR was profound (FIGS. 12A and 13C). However, both the 691534 (FIGS. 12B and 13B) and BJ18 (FIGS. 12D and 13D) epitopes of CD-44 were highly expressed in the cells.

Figure 14:
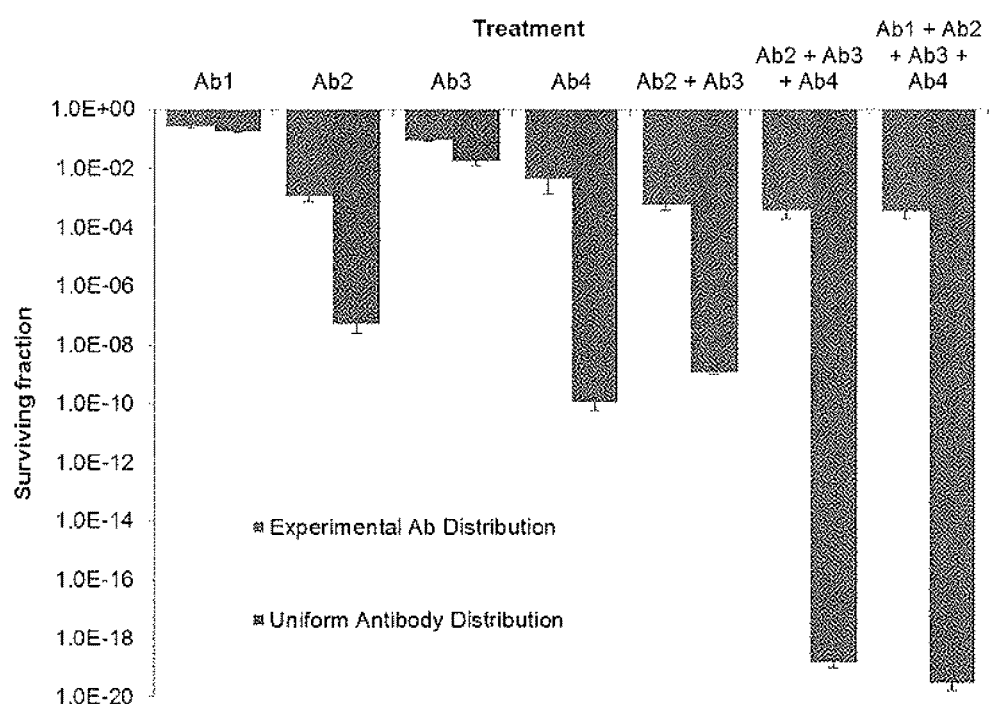
FIG. 14 shows dependence of surviving fraction on distribution of antibody binding among targeted cells and on constituents of antibody cocktail (concentration, 1.0 µg/mL). Antibodies were armed with $^{211}$At at specific activity of 4.25×10$^{15}$ Bq/mol. Mean surviving fraction with SE are displayed (n=3; for Ab3, n=2). Large differences in surviving fraction arise when experimentally measured distributions are compared with assumed uniform distribution.
Figure 15:
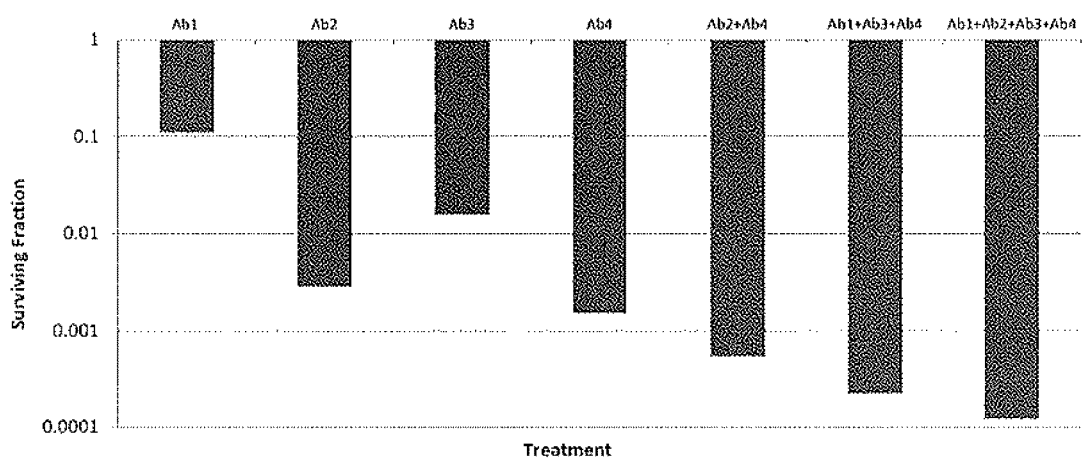
FIG. 15 shows Monte Carlo-derived surviving fraction of MDA-MB-231 cells for select antibody treatments.

Results for selected permutations of the antibody cocktail are shown in FIG. 14. The surviving fractions that arise when it is assumed that each radiolabeled antibody is uniformly distributed among the targeted population are lower than those when the experimentally measured lognormal distribution is used. When the best individual antibody is compared with the quadruple cocktail, over a log of kill is gained (FIG. 15). Even adding a single antibody to the best individual antibody results in increased cell killing. To determine whether or not this additional killing is a result of a change in the absorbed dose distribution in the combined treatments, histograms of absorbed dose to the cells treated with different permutations of the cocktail were plotted (FIG. 16). Adding additional antibodies changed the distribution of uptake in the cell population, resulting in up to a several-fold increase in the absorbed dose to the least-irradiated cells when compared to the absorbed doses obtained with the best single antibody treatment.

When either remaining antibody was added to the best postsaturation double cocktail (Ab2 and Ab3), the surviving fraction decreased at all concentrations (FIG. 17). The triplet combination of Ab1, Ab2, and Ab4 performed approximately as well as the best postsaturation double-antibody cocktail at all concentrations. Additionally, the quadruple-antibody cocktail performed as well as or better than all triple cocktails at all tested concentrations. The dependence of surviving faction on antibody distribution was assessed for the different cocktail combinations at 1.0 μg/mL. The SFs derived from experimentally measured antibody distributions were compared with those from assumed uniform antibody distributions, in which each cell received the mean absorbed dose to the respective populations (FIG. 14). The surviving fraction for the uniform distribution was significantly lower than the respective surviving fraction for the non-uniform experimental distribution for all combinations studied. As the number of the antibodies in the cocktail increased, so did the discrepancy between the surviving fractions for the uniform distribution and the non-uniform experimental distribution.

Furthermore, the dependence of cell killing on the specific activity of the $^{211}$At-labeled antibodies was studied. In this context, the efficacy of antibody cocktails versus a single antibody was compared by holding the total antibody concentration constant (3.0 μg/mL) while varying the specific activity of the $^{211}$At-labeled antibodies. Accordingly, single-antibody treatments were analyzed at 3.0 μg/mL, and antibody cocktails comprised 3 antibodies, each at 1.0 μg/mL. Cocktails were compared with Ab2 alone (FIG. 20A) and Ab4 alone (FIG. 20B) because they emerged as the most effective single-antibody treatments (FIG. 17) Similar analyses were performed for $^{213}$Bi and $^{225}$Ac, shown in Tables 1 and 2 supra.

Figure 16C:
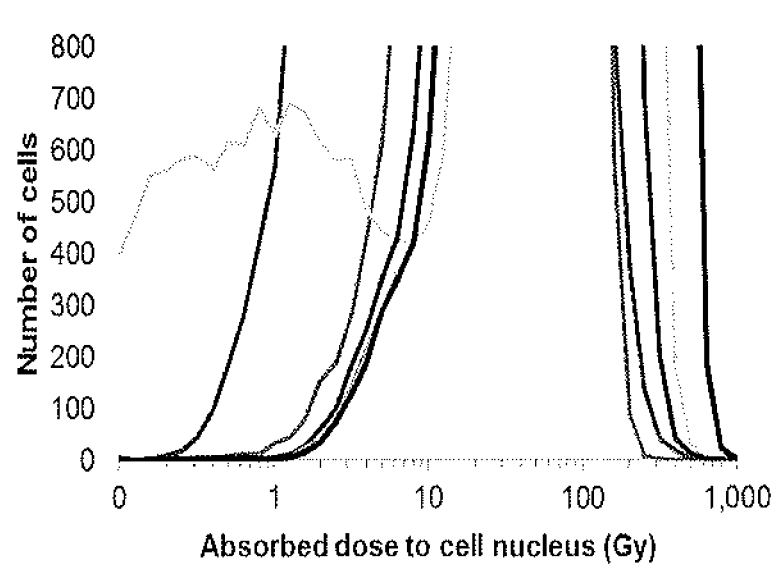
Figure 17C:
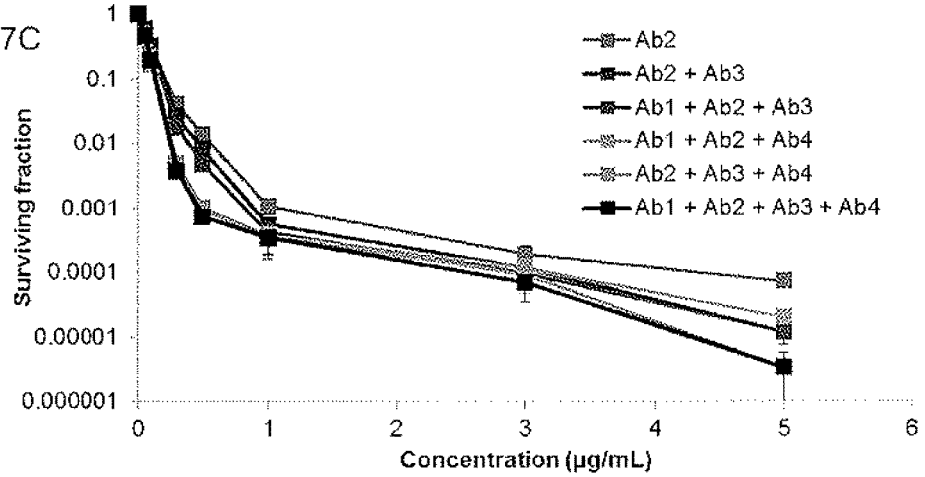
Figure 21:
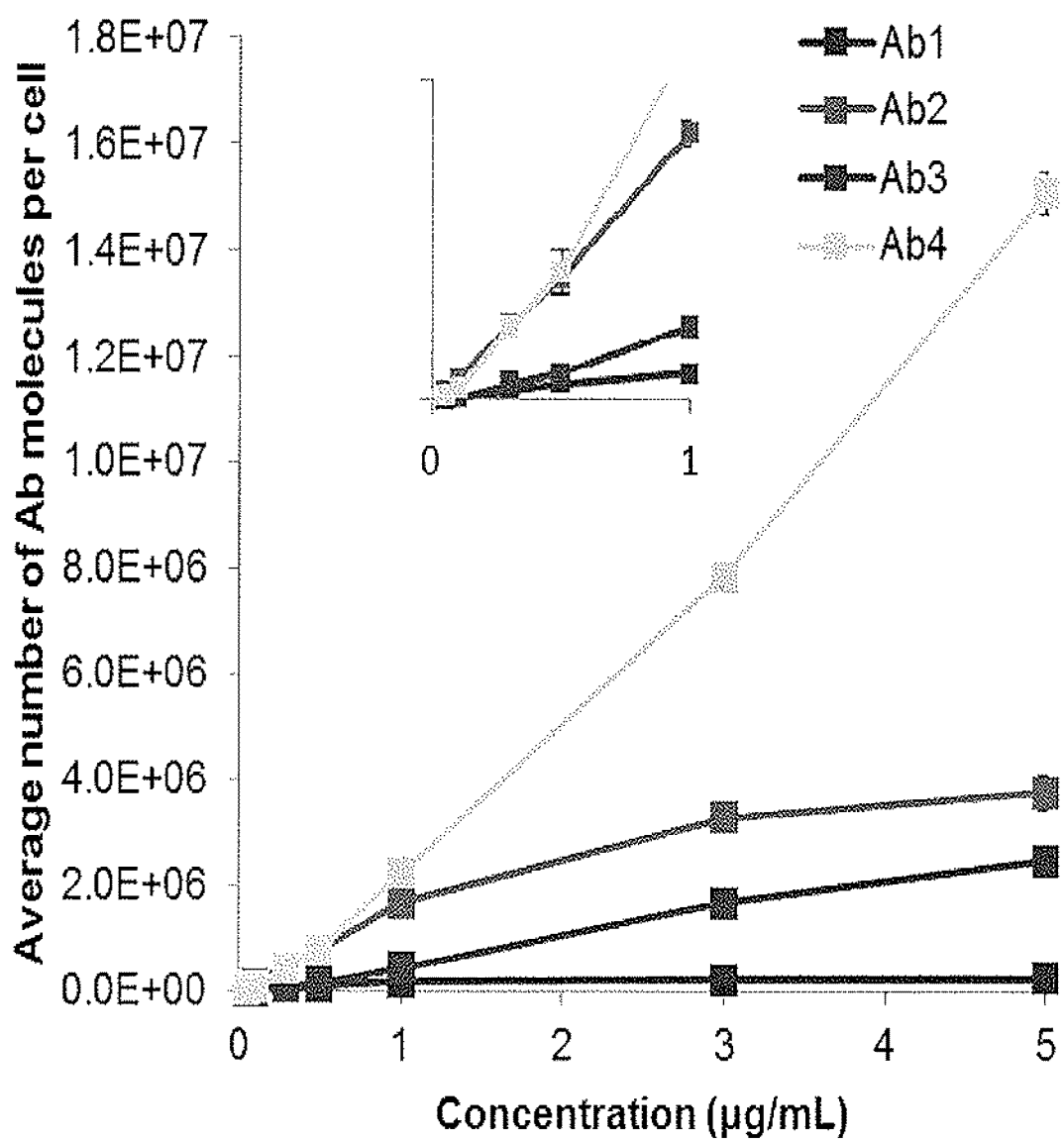
FIG. 21 shows mean number of antibody molecules bound per cell with SE (n=3; for Ab3, n=2) as function of concentration of antibodies in cocktail. SEs fit within symbols. Inset zooms in on low-concentration region (<1 µg/mL) to demonstrate linearity in this region.

With the exception of Ab4, the mean levels of antibody binding to MDA-MB-231 cells began to saturate with increasing concentration at about 1.0 μg/mL (FIG. 21) This is reflected in the survival curves that correspond to single-antibody treatments (FIG. 17C). These curves begin to saturate at about 1.0 μg/mL as well. This parallels observations made by Example 1. The saturation in the Ab4 curve occurred despite the linear increase in mean antibody binding over the entire concentration range studied. As shown in FIG. 16C, this can be attributed to insufficient targeting of a small subpopulation of cells that have low antibody binding. These cells receive much lower absorbed doses than the other cells in the population, which dramatically increases their probability of survival. This also explains why Ab2 attains a higher degree of cell kill than Ab4 (FIG. 17A), despite the apparent advantage of Ab4 in FIG. 21.

Figure 16A:
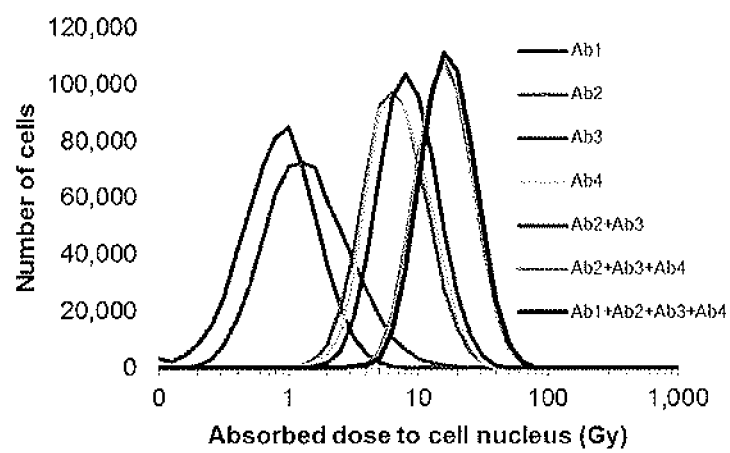
FIGS. 16A, 16B and 16C shows Histograms depicting distributions of absorbed dose to MBA-MB-231 cells exposed to different permutations of antibody cocktail at 0.5 µg/mL (FIG. 16A) and 3.0 µg/mL (FIG. 16B).
Figure 16B:
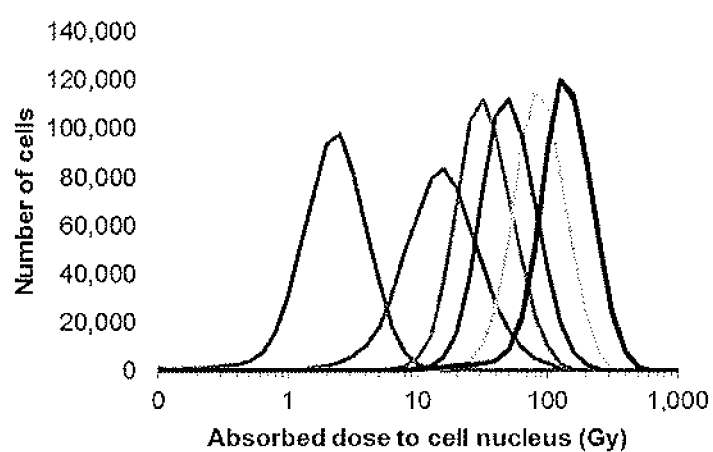

Comparison of FIGS. 16A and 16B show that increasing the concentration from 0.5 to 3 μg/mL narrowed the distribution, a phenomenon observed in Example 1. As antibodies were added to the cocktail, at both presaturation (0.5 μg/mL, FIG. 16A) and postsaturation (3 μg/mL, FIG. 16B) concentrations, the shape of the absorbed dose distribution curve became taller and narrower.

At the pre-saturation antibody concentration, 0.5 μg/mL, the least irradiated cells in the single-antibody treatments received absorbed doses ranging from 0.1 to 1.0 Gy. The least irradiated cells treated with the different combinations of the cocktail received larger doses, with the triple- and quadruple-cocktail treatments delivering 3-4 Gy (FIG. 16A). This concentration is significant as indicated by the increased cell killing that can be achieved, at this concentration, when cells are treated with the antibody cocktails compared with a single antibody (FIG. 17A). Similar observations could be made at the postsaturation concentration of 3 μg/mL, albeit at considerably higher absorbed doses (FIG. 16B and FIG. 17B). The triple-antibody cocktail had an absorbed dose distribution almost identical to the quadruple-antibody cocktail (FIG. 16B). At this concentration, it appears that Ab1 had little effect when combined with the 3 other antibodies. However, Ab1 had a slightly more observable contribution at the presaturation concentration (FIG. 16A).

To focus on the impact of antibody distribution among the target cell population, dosimetry calculations assumed cell surface binding of antibodies and no biologic clearance from the cell or internalization within the cell. Anti-CD44, anti-EGFR, and anti-CD73 internalize on binding to cell surface receptors. This would increase the S values (i.e., dose per decay) beneficially by up to a factor of 6 depending on whether the radionuclide is shuttled to the nucleus. However, more importantly, the biologic clearance may be affected adversely, particularly in the case of Astatine-211, because halogens are metabolized by cells once internalized. Similarly, the decay of Actinium-225 to its daughters may result in their departure from the cell, which would have a substantial impact on the dose delivered. Although these factors can play a major role in the distribution of absorbed dose among the targeted population, they are moot in the absence of an initial targeting distribution that is therapeutically viable.

Based on the shape of the distributions of fluorescence, and thus antibody molecules on the population of labeled cells, it appears that the binding of anti-EGFR, anti-CD-44, anti-CD-73, and anti-CD-44 on the surface of MDA-MB-231 cells was reasonably lognormal (FIG. 11 and FIG. 12). Anti-CD-44 deviated from lognormal quite remarkably at the low expression end of the spectrum (FIG. 16C). This was also observed for anti-CD20 and anti-TP3 in other cell lines. Absorbed dose estimates often assume a uniform distribution by simply considering the mean. FIG. 14 compares the response of MDA-MB-231 cells with cocktails of $^{211}$At-labeled antibodies when absorbed dose distributions were calculated on the basis of the observed lognormal distribution versus an assumed uniform distribution.

Surprisingly and significantly, far more cell killing was afforded by the uniform distribution than the experimental lognormal distributions, with up to a 16-log difference. This indicates that the lognormal antigen distribution among a cancer cell population is a substantial hurdle to overcome in radioimmunotherapy because it can be difficult to eradicate isolated tumor cells. This emphasizes the need to assess the distribution of each antigen to be targeted. Furthermore, cocktails of antibodies can improve targeting and thus cell killing with radioimmunotherapy, enhancing the effectiveness of the therapy (FIG. 14). The role of radiolabeled antibody cocktails is not limited to treating DTCs but is also important when treating very small micrometastases for which lognormal activity distributions of a emitters can affect the response of the cell population. As the size of the micrometastasis increases, the nonuniformity of the activity distribution may be dominated by issues related to the absence of sufficient penetration into the core.

Figure 20A:
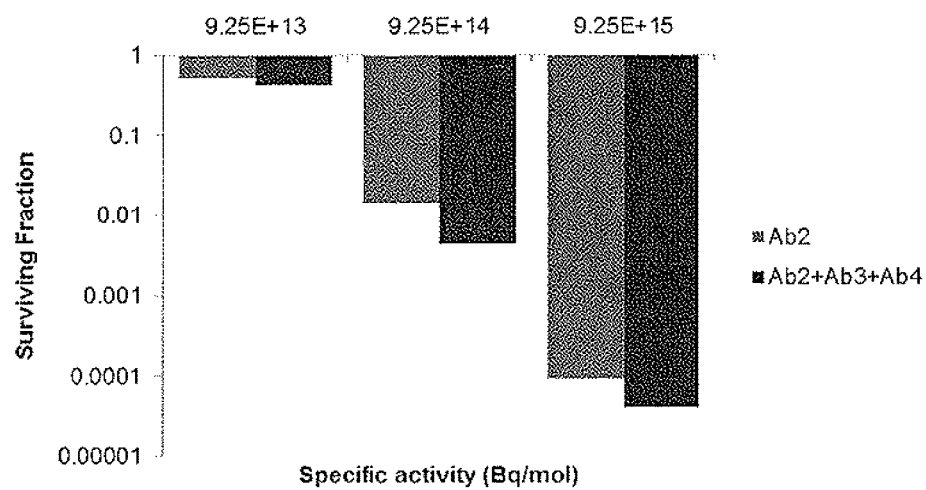
FIGS. 20A and 20B shows a comparison of cell killing with single antibodies vs. cocktails of antibodies when total antibody concentration is held constant and specific activity of $^{211}$At-labeled antibodies is varied. Concentration is 3.0 µg/mL for single antibodies and 1.0 µg/mL for antibodies in cocktails, such that all treatments have total antibody concentration of 3.0 µg/mL. Cocktails were compared with Ab2 (FIG. 20A) and Ab4 (FIG. 20B).
Figure 20B:
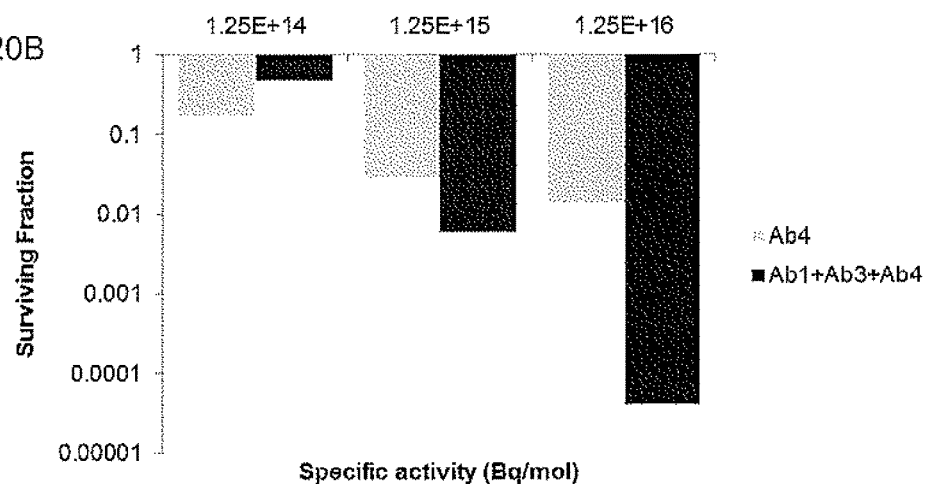

Specific activity is an important determinant in radioimmunotherapy. However, the role of specific activity in determining the relative advantage of cocktails of radiolabeled antibodies relative to single radiolabeled antibodies has not been explored. FIG. 20A provides insight into the critical role that specific activity plays in this assessment. When cell survival after treatment with $^{211}$At-labeled Ab2 alone is compared with a cocktail of $^{211}$At-labeled Ab2, Ab3, and Ab4 at a fixed total antibody concentration of 3 µg/mL, it is apparent that the added benefit of the cocktail was modest regardless of the specific activity (FIG. 20A). The relative advantage, defined as the ratio of the SFs resulting from the different treatments, was only 1.26-, 2.67-, and 1.38-fold for specific activities of $9.25 \times 10^{13}$, $9.25 \times 10^{14}$, and $1.25 \times 10^{16}$ Bq/mol, respectively, as shown in Table 1, supra. However, when $^{211}$At-labeled Ab4 alone is compared with a cocktail of $^{211}$At-labeled Ab1, Ab3, and Ab4 at a fixed total antibody concentration of 3 µg/mL, the relative advantage could be substantial (FIG. 20B). Relative advantages of 0.34-, 2.83-, and 244-fold were obtained for specific activities of $1.25 \times 10^{14}$, $1.25 \times 10^{15}$, and $1.25 \times 10^{16}$ Bq/mol, respectively, as shown in Table 2, supra. The large enhancement at the highest specific activity can be attributed to the increased capacity of Ab1 and Ab3 to contribute to the sterilization of the small population of cells with low Ab4 antigen density (FIG. 16C) when the specific activity was raised. This high specific activity is achievable and values as high as 1 GBq/mg (~$1.6 \times 10^{17}$ Bq/mol) for $^{211}$At-trastuzumab have been obtained. If limited to specific activities of only $1.25 \times 10^{14}$ Bq/mol, then Ab4 alone is preferred. Similar results could be seen when the antibodies were labeled with $^{213}$Bi or $^{225}$Ac. For the mid-level and higher specific activities when Ab4 was used as the baseline for comparison, the cocktail was highly advantageous (Table 2, supra). When Ab2 was used as the baseline, the cocktail could have a modest benefit depending on the specific activity (Table 1, supra).

The invention has been described via the specific embodiments and examples provided above which, however, do not limit the invention in any way.

What is claimed is:

1. A therapeutic composition for treating diseased cells in a patient comprising a plurality of therapeutic agents selected from the group consisting of radiopharmaceuticals, chemotherapeutic agents and radionuclide labeled antibodies, wherein the selection of and the relative concentrations of the therapeutic agents in the composition is determined by a method including the steps of:
   (a) exposing populations of the diseased cells to increasing concentrations of combinations of the therapeutic agents, to increasing concentrations of the individual therapeutic agents, or both;
   (b) measuring the incorporation by cellular uptake of the therapeutic agents or the therapeutic agent combinations;
   (c) plotting the number of cells vs the amount of incorporated therapeutic agents to obtain distribution plots for the cell populations;
   (d) predicting the surviving fractions of the cell populations employing a simulation that uses the therapeutic agent distribution plots and a function that expresses the probability that a given cell will survive a given amount of an incorporated therapeutic agent; and
   (e) selecting the therapeutic agent combination and relative concentration of each agent within the selected combination predicted to be most lethal.

2. The composition of claim 1 wherein said simulation comprises a Monte Carlo simulation.

3. The composition of claim 2, wherein the Monte Carlo simulation accounts for the amount of each agent in each cell and the results are used to identify the most effective combination of therapeutic agents, and their therapeutically optimal doses in combination.

4. The composition of claim 1, wherein said individual patient's cells comprise cancer cells.

5. The composition of claim 1, wherein said incorporation of said therapeutic agent is measured using a high-speed technique.

6. The composition of claim 5, wherein said high-speed technique comprises fluorescence spectroscopy.

7. The composition of claim 6, wherein the fluorescence measurement comprises the mean fluorescence intensity (MFI).

8. The composition of claim 5, wherein the high-speed technique for assaying therapeutic agent incorporation on a cell-by-cell basis comprises flow cytometry.

9. The composition of claim 5, wherein the high-speed technique for assaying therapeutic agent incorporation on a cell-by-cell basis comprises fluorescence microscopy or laser scanning microscopy.

10. The composition of claim 2, wherein said Monte Carlo simulation comprises flow-cytometry-assisted Monte Carlo simulation.

11. The composition of claim 2, wherein said Monte Carlo simulation comprises fluorescence microscope-assisted Monte Carlo simulation or laser scanning microscope-assisted Monte Carlo simulation.

12. The composition of claim 1, wherein the therapeutic agents are selected from a plurality of radionuclide labeled antibodies, and the relative concentrations of the radionuclide labeled antibodies in the composition is determined by a method including the steps of:
   (a) exposing populations of the diseased cells to increasing concentrations of combinations of the radionuclide labeled antibodies, to increasing concentrations of the individual radionuclide labeled antibodies, or both;
   (b) measuring the incorporation by cellular uptake of the radionuclide labeled antibodies or the radionuclide labeled antibody combinations;
   (c) plotting the number of cells vs the amount of incorporated antibodies to obtain distribution plots for the cell populations;
   (d) predicting the surviving fractions of the cell populations employing a simulation that that uses the calculated incorporation of the antibodies in each cell and a function that expresses the probability that a given cell will survive upon incorporating a cellular radiation dose characteristic of the radionuclide of the incorporated antibody; and
   (e) selecting the radionuclide labeled antibody combination and relative concentration of each antibody within the selected combination predicted to be most lethal.

13. The composition of claim 12, wherein said simulation comprises a Monte Carlo simulation.

14. The composition of claim 13, wherein the Monte Carlo simulation accounts for the amount of each agent in each cell and the results are used to identify the most effective combination of therapeutic agents, and their therapeutically optimal doses in combination.

15. The composition of claim 12, wherein said individual patient's cells comprise cancer cells.

16. The composition of claim 13, wherein said Monte Carlo simulation comprises flow-cytometry-assisted Monte Carlo simulation, fluorescence microscope-assisted Monte Carlo simulation or laser scanning microscope-assisted Monte Carlo simulation.

17. The composition of claim 1, wherein the therapeutic agents are selected from a plurality of radionuclide labeled antibodies, and the relative concentrations of the radionuclide labeled antibodies in the composition is determined by a method including the steps of:

(a) exposing populations of the diseased cells to increasing concentrations of combinations of the radionuclide labeled antibodies, to increasing concentrations of the individual radionuclide labeled antibodies, or both;
(b) determining the number of antibodies bound to individual diseased cells;
(c) predicting the surviving fractions of the cell populations employing a simulation that that uses the therapeutic agent distribution plots and a function that expresses the probability that a given cell will survive a given amount of an incorporated therapeutic agent; and
(d) selecting the therapeutic agent combination and relative concentration of each agent within the selected combination predicted to be most lethal.

18. The composition of claim 17, wherein determining the number of antibodies bound to individual diseased cells is accomplished by the steps of (i) measuring fluorescence intensity and (ii) calculating absorbed dose to each cell.

19. The composition of claim 18, wherein the step (i) of measuring fluorescence intensity utilizes Bang's beads.

20. The composition of claim 18, wherein the simulation comprises a Monte Carlo simulation.

21. The composition of claim 20, wherein the Monte Carlo simulation is modified to account for specific activity of the antibodies.

22. The composition of claim 20, wherein the Monte Carlo simulation is further modified to account for the calculated absorbed dose to each cell.

23. The composition of claim 17 wherein the diseased cells comprise cancer cells.

* * * * *